United States Patent
Hruby et al.

(10) Patent No.: US 10,188,704 B2
(45) Date of Patent: Jan. 29, 2019

(54) ENHANCED MELANOMA CANCER PREVENTION BY NOVEL MELANOTROPINS

(71) Applicant: ARIZONA BOARD OF REGENTS ON BEHALF OF THE UNIVERSITY OF ARIZONA, Tucson, AZ (US)

(72) Inventors: Victor J. Hruby, Tucson, AZ (US); Minying Cai, Tucson, AZ (US)

(73) Assignee: ARIZONA BOARD OF REGENTS ON BEHALF OF THE UNIVERSITY OF ARIZONA, Tucson, AZ (US)

(*) Notice: Subject to any disclaimer, the term of this patent is extended or adjusted under 35 U.S.C. 154(b) by 0 days.

(21) Appl. No.: 15/574,794

(22) PCT Filed: May 18, 2016

(86) PCT No.: PCT/US2016/033010
§ 371 (c)(1),
(2) Date: Nov. 16, 2017

(87) PCT Pub. No.: WO2016/187264
PCT Pub. Date: Nov. 24, 2016

(65) Prior Publication Data
US 2018/0140677 A1    May 24, 2018

Related U.S. Application Data

(60) Provisional application No. 62/162,997, filed on May 18, 2015.

(51) Int. Cl.
| | | |
|---|---|---|
| A61K 38/00 | (2006.01) | |
| A61K 38/34 | (2006.01) | |
| A61K 8/64 | (2006.01) | |
| C07K 14/685 | (2006.01) | |
| C07K 14/69 | (2006.01) | |
| A61Q 19/04 | (2006.01) | |
| A61K 38/10 | (2006.01) | |
| C07K 7/08 | (2006.01) | |

(52) U.S. Cl.
CPC .............. *A61K 38/34* (2013.01); *A61K 8/64* (2013.01); *A61K 38/10* (2013.01); *A61Q 19/04* (2013.01); *C07K 7/08* (2013.01); *C07K 14/685* (2013.01); *C07K 14/69* (2013.01); *A61K 38/00* (2013.01)

(58) Field of Classification Search
None
See application file for complete search history.

(56) References Cited

U.S. PATENT DOCUMENTS

| | | |
|---|---|---|
| 4,559,157 A | 12/1985 | Smith et al. |
| 4,608,392 A | 8/1986 | Jacquet et al. |
| 4,820,508 A | 4/1989 | Woltzman |
| 4,938,949 A | 7/1990 | Borch et al. |
| 4,992,478 A | 2/1991 | Geria |
| 5,167,649 A | 12/1992 | Zook |
| 7,638,558 B2 | 12/2009 | Breitenkamp et al. |
| 2009/0176712 A1 | 7/2009 | Haskell-Luevano et al. |

FOREIGN PATENT DOCUMENTS

| | | |
|---|---|---|
| WO | WO1982000031 A1 | 1/1982 |
| WO | WO2014081845 A2 | 5/2014 |

OTHER PUBLICATIONS

Barkey N M et al., "Development of Melanoma Targeted Polymer Micelles by Conjugation of a Melanocortin 1 Receptor (MC1R) Specific Ligand," J. Med. Chem., Oct. 2011, 54:8078-8084.
Cevc et al., Biochimica et Biophysica Acta, Jan. 19, 1998;1368(2):201-15.

*Primary Examiner* — Jeanette M Lieb
(74) *Attorney, Agent, or Firm* — Nguyen & Tarbet Law Firm

(57) ABSTRACT

A gamma-melanocyte stimulating hormone (γ-MSH) derivative having improved stability, selectivity and bioavailabilty. The γ-MSH derivative is selective for the melanocortin-1 receptor (MC1 R) and is deliverable to skin cells via topical or transdermal delivery. The γ-MSH derivative is made up of naturally occurring amino acids for stimulating melanin from within for photoprotection of human skin against ultraviolet radiation damage.

20 Claims, 2 Drawing Sheets

Specification includes a Sequence Listing.

Half life= 52 min

ENHANCED MELANOMA CANCER PREVENTION BY NOVEL MELANOTROPINS

CROSS REFERENCE

This application claims priority to U.S. Provisional Patent Application No. 62/162,997, filed May 18, 2015, the specification(s) of which is/are incorporated herein in their entirety by reference.

GOVERNMENT SUPPORT

This invention was made with government support under Grant No. R01 DK017420 and R01 GM108040 awarded by NIH. The government has certain rights in the invention.

FIELD OF THE INVENTION

The present invention relates to melanocyte stimulating hormones (MSH), in particular, melanotropin ligands having improved selectivity, stability, and bioavailability.

BACKGROUND OF THE INVENTION

There is a critical medical need for prevention of skin damage and development of melanoma and other cancer cells in the human skin caused by ultraviolet (UV) chemical damage to DNA in the cell. Skin cancer is the most commonly diagnosed cancer in the US, and an estimated 76,380 new cases of melanoma will be diagnosed in the US in 2016. Current efforts to prevent UV damage to human skin, which in many cases leads to melanoma and other skin cancers, is primarily limited to using lotions containing organic compounds that absorb light in the UV absorption regions of the electromagnetic spectrum (200-800 nM). Although this approach has some success, the use of lotions is an overall failure due to the inadequacies of the lotions or the improper or inadequate use of these lotions. It has been observed that when dark- and light-skinned persons both spend significant time in the sun, dark-skinned persons have a much lower risk of developing melanoma. Internally simulated photo-protection of human skin would provide a more effective path to sun protection and cancer prevention than currently available via sunscreen lotions.

Melanocyte stimulation hormones (MSH), also known as melanotropins, are products of the natural precursor protein, propiomelanocortin (POMC), which is found in all terrestrial animal life and is responsible for both skin and hair color in animal life. MSH consists of α-melanocyte-stimulating hormone (α-MSH), β-melanocyte-stimulating hormone (β-MSH), and γ-melanocyte-stimulating hormone (γ-MSH). The melanocortin 1 receptor (MC1R), also known as a melanocyte-stimulating hormone receptor, a melanin-activating peptide receptor, or a melanotropin receptor, is a protein that can bind to MSH, and is known to regulate pigmentation for the skin. When MC1R is activated, it can trigger melanocytes to produce eumelanin, which is a type of melanin that can protect the skin from damage caused by UV radiation in sunlight. The γ-MSH is one of a family of naturally occurring peptide hormones that are released by skin cells in response to the damaging rays of UVR. Because γ-MSH has higher affinity for MC1R, while showing less affinity for MC3R, MC4R, and MC5R receptors, it almost exclusively induces melanin production. As it is more selective for MC1R, γ-MSH can have less negative side effects than the other family members, α-MSH and β-MSH.

The present invention features organic peptides related to the melanocyte stimulation hormone. These compounds are the most selective for the relevant hMC1R. The target peptide γ-MSH is modified to improve its properties as a cancer preventive to make γ-MSH more stable, more MCR1 selective, and more readily bioavailable for topical or transdermal delivery.

Studies have shown that "skin tanning (pigmentation)" by the native hormone α-MSH and especially by a more stable analogue [Nle4, D-Phe7] α-MSH (NDP-α-MSH) protects against UV damage to the skin of normal humans, including those who do not pigment well in response to UV radiation (UVR). Hence, the present invention provides an innovative approach to promote the natural pigmentation of skin without exposure to sunlight with a peptide ligand that is selective for the hMC1R and therefore will have no side effects (toxicities). Moreover, because the present invention internally stimulates photo-protection of human skin, it provides a more effective path to UVR protection and cancer prevention than the protection currently available from commercial chemical sunscreens (lotions, sprays, etc.) and it does not rely on multi or daily reapplications.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

It is an objective of the present invention to provide for analogues of γ-MSH that are more stable, more selective for the melanocortin-1 receptor (MC1R), and more bioavailable, as specified in the independent claims. Embodiments of the invention are given in the dependent claims. Embodiments of the present invention can be freely combined with each other if they are not mutually exclusive.

In one embodiment, the subject disclosure features a modified melanocortin 1 receptor (MC1R) peptide ligand comprising naturally occurring amino acids, the MC1R peptide ligand being a derivative of γ-MSH. According to one embodiment, the MC1R peptide ligand can be according to SEQ ID NO. 1:

(SEQ ID NO: 1)
H-Tyr$^1$-Val$^2$-Waa$^3$-Gly$^4$-Xaa$^5$-Phe$^6$-Yaa$^7$-Zaa$^8$-Asp$^9$-Arg$^{10}$-Phe$^{11}$-Gly$^{12}$-R1.

In some embodiments, Waa is a Met, Ile, or Leu; Xaa is a His or Pro; Yaa is an Arg or Leu; and Zaa is a Phe or Trp. In other embodiments, R1 of the C-terminal is —NH$_2$, or —OH. Preferably, Waa is not Met, Xaa is not His, Yaa is not Arg, Zaa is not Trp, and R1 is not —OH simultaneously. It is also preferable that the MC1R peptide ligand is selective for and an agonist of MC1R such that the MC1R peptide ligand is capable of stimulating melanin production.

An inventive technical feature of the present invention is that the MC1R peptide ligand is highly selective for MC1R. Without wishing to limit the invention to any theory or mechanism, this is advantageous because by delivering γ-MSH derivatives to skin cells via tropical or transdermal delivery, the γ-MSH derivatives agonizes the MC1R and photo-protection of human skin against UVR damage occurs by the stimulation of melanogenesis from within, thereby acting as a cancer preventative. The need for exposure to natural or artificial sunlight to stimulate melanin synthesis is thereby eliminated.

DESCRIPTION OF PREFERRED EMBODIMENTS

Figure 1:
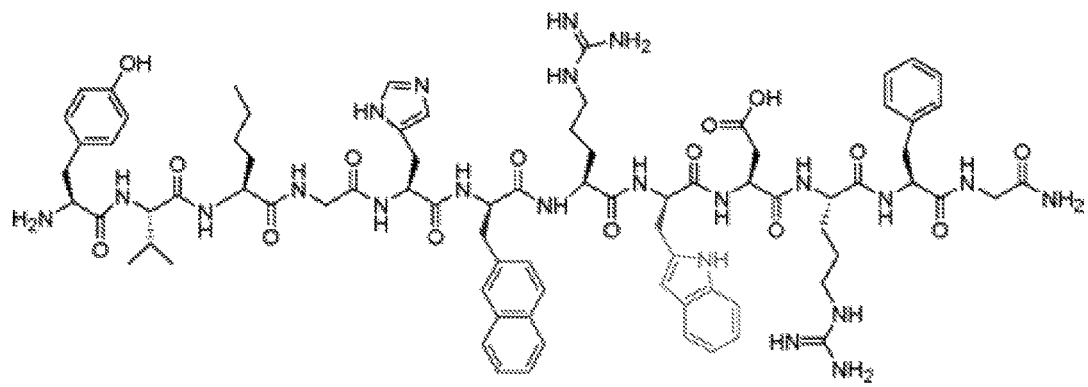
FIG. 1 shows a non-limiting exemplary structure of a selective hMC1R analogue (SEQ ID NO. 11) of the present invention.

In general, unless otherwise specified, the abbreviations used for the designation of amino acids and the protective groups used therefore are based on recommendations of the IUPAC-IUB Commission of Biochemical Nomenclature (Biochemistry, 11:1726-1732 (1972)). The nomenclature used to define compounds of the invention is that specified by IUPAC, published in European Journal of Biochemistry, 138:9-37 (1984). With regard to certain amino acids disclosed herein, their structures and abbreviations are apparent from the peptide structures such as that shown in FIG. 1 and the peptides provided in Table 1.

As used herein, the term "natural amino acids" refers to the twenty amino acids that are found in nature, i.e. occur naturally. The natural amino acids are as follows: alanine, arginine, glycine, asparagine, aspartic acid, cysteine, glutamine, glutamic acid, serine, threonine, histidine, lysine, methionine, proline, valine, isoleucine, leucine, tyrosine, tryptophan, and phenylalanine. This application adheres to the IUPAC rules of standard abbreviations for amino acids.

The letter "D" preceding any three-letter abbreviation for an amino acid, e.g. as in "D-Nal" or "D-Phe," denotes the D-form of the amino acid. The letter "L" preceding an amino acid three-letter abbreviation denotes the natural L-form of the amino acid. For purposes of this disclosure, unless otherwise indicated, absence of a "D" or "L" designation indicates that the abbreviation refers to both the D- and L-forms. Where the common single-letter abbreviation is used, capitalization refers to the L-form and small letter designation refers to the D-form, unless otherwise indicated. For each amino acid, an additional conservative substitution includes the "homolog" of that amino acid, where the "homolog" is an amino acid with a methylene group ($CH_2$) inserted into the side chain at the beta position of that side chain. Examples of such homologs include, without limitation, homophenylalanine, homoarginine, homoserine, and the like. As used herein, a "peptide," is defined as an amino acid sequence from three amino acids to about 700 amino acids in length. As known to one of ordinary skill in the art, a "ligand" is a molecule which produces a signal by binding to a site on a target protein.

As used herein, an "MC1R peptide ligand" refers to a compound with affinity for melanocortin receptors, particularly melanocortin 1 receptors (MC1R or hMC1R), that can result in measurable biological activity in cells, tissues, or organisms that contain the MC receptor.

Related peptides includes allelic variants; fragments; derivatives; substitution, deletion, and insertion variants; fusion polypeptides; and orthologs; and each amino acid of each such related peptide may be either natural or unnatural of the "D" or "L" configuration which corresponds to the stereochemical designation "S" and "R," respectively, as defined in the RS system of Cahn et al., (Pure Applied Chemistry, 45:11-30 (1974), and references cited therein). Such related peptides may be mature peptides, i.e., lacking a signal peptide.

As defined herein, the term "agonist" refers to compound that enhances a response. The agonist binds to the same site as the endogenous compound and produces the same type of signal, usually of equal or greater magnitude than the endogenous agent. As defined herein, the term "antagonist" refers to compound that binds to the same site as the endogenous compound and diminishes or blocks the signal generated by the endogenous agent.

As used herein, R1 refers to the functional group linked to the carbonyl at the C-terminus of the peptide ligand. Typically, the C-terminus is a carboxylic acid, hence, R1 is an —OH group. In some embodiments, the C-terminus may be modified. For example, C-terminal modification by amidation results in R1 being an —$NH_2$. Without wishing to limit the invention to a particular theory or mechanism, C-terminal modifications, such as amidation, can enhance the biological activity of the peptide ligand, increase the ligand's stability, efficacy, and ability to enter cells, as well as increase its ability to resist enzymatic degradation.

Embodiments of the invention may feature an MC1R peptide ligand comprising a reactive functional group towards a complementary functional group on a moiety such as a small molecule, a polymer or a functionalized surface, for example a functional group on the polymer shell of an in vivo stable micelle. The MC1R peptide ligand may comprise a functional group that allows attachment via a Huisgen 1,3-dipolar cycloaddition, Diels-Alder reaction, or any other reaction that has the features of "click" chemistry to a complementary functional group on the moiety. Click chemistry involves a reaction that displays selectivity and high conversion, generally although not necessarily, without driving the reaction by removal of a side product. In addition to use with a polymer shell of a micelle, the MC1R peptide ligand can be attached as end groups or side groups of a water soluble or water suspendable homopolymer or copolymer. The homopolymer or copolymer can be linear, branched, hyperbranched, dendritic, or a network. The copolymer can be a random copolymer, block copolymer, or graft copolymer. Surfaces can be that of a particle, including polymeric, ceramic, glass, or metal where the surface is flat or irregular including within the pores of a solid porous material. The dimensions of particles can be in the nanometer, micrometer or of larger dimensions.

The MC1R peptide ligand can be coupled via a linking group to a small molecule, polymer or functionalized surface that includes a contrast agent (e.g., imaging contrast agent) or a therapeutic agent by a stable or biodegradable linker. The contrast agents can include: near infrared (NIR) fluorescent dyes, such as ICG derivatives; CT contrast agents, such as gold; MRI or SPECT contrast agents, such as Gd, Tc99m, and $^{111}$In chelates; radiotherapy agents, such as Yttrium; PET imaging agents comprising, for example, 18-F, 11-C, 18-O, or Gallium 64; alkylating chemotherapy agents, such as melphalan or ifosfamide; and compounds for systemic melanoma chemotherapies, such as dacarbazine, paclitaxel, and vincristine.

In some embodiments of the invention, the MC1R peptide ligand is attached to a stable micelle (an MC1R peptide ligand-micelle complex) comprising a diblock, triblock or tetrablock copolymer that self organizes into: an inner core comprising a hydrophobic block that provides an environment where a drug or other agent can reside within the micelle; an outer core comprising an intermediate unit or block comprising at least one group that crosslinks, hence stabilizing the micelle; and a hydrophilic shell comprising a water soluble polymer with a functional group distal to the core. The functional group may be used to attach the targeting MC1R-ligand. Micelles of this type are disclosed in Breitenkamp, et al., U.S. Pat. No. 7,638,558, and incorporated herein by reference.

The crosslink of the outer shell can be a chemical crosslink which comprise one or more covalent bonds or a physical crosslink that involve associated functional groups or ions, which bind by ligation of ions, dipolar interactions, or any other intermolecular forces. The crosslink can be a disulfide, ester, hydrazone, Schiff base, zinc complexation, Iron (III) complexation, or other crosslinking that can be reversible. In embodiments of the invention, the crosslink is stable in vivo at a normal pH exhibited in most normal cells but uncrosslinks at the lower pH of a malignant cell that is targeted, permitting delivery of a payload to a desired anatomical site, such as a tumor site, through a pH-triggered mechanism. Barkey N M et al., "Development of Melanoma Targeted Polymer Micelles by Conjugation of a Melanocortin 1 Receptor (MC1R) Specific Ligand," J. Med. Chem., October 2011, 54:8078-8084, which describes the formation of embodiments of MC1R peptide ligand-micelle complexes of the invention, is incorporated herein by reference in its entirety.

Water soluble, hydrophilic, polymers that can be used include polyethyleneoxide (also referred to as polyethylene glycol or PEG), poly(N-vinyl-2-pyrolidone), poly(N-isopropylacrylamide), poly(hydroxyethyl acrylate), poly(hydroxylethyl methacrylate), poly(N-(2-hydroxypropoyl)methacrylamide) (HMPA), or any derivatives thereof. Such water soluble polymers are prepared in a manner such that the distal end to the core has a reactive functionalized that is complementary to a reactive functional group on the targeting MC1R peptide ligand.

In an embodiment of the invention, the micelle has an inner core that comprises a poly(amino acid) block where a sufficient proportion of the amino acid repeating units have a hydrophobic side group to render the block hydrophobic. The amino acids can be natural or unnatural. The amino acids can include phenylalanine, alanine benzyl glutamate, alkyl glutamate, benzyl aspartate, alkyl aspartate, leucine, tyrosine, serine, threonine, glutamic acid, aspartic acid, or a combination thereof.

In some embodiments of the invention, the micelle has an outer core comprising a reactive functional group that can be combined with a like reactive functional group to form a crosslink. For example, a pair of thiol functional groups can be combined to form a disulfide. The combined functional groups can be with the inclusion of a di-substituted coupling reagent. For example, a carboxylic acid functional group can be combined with a divalent or polyvalent salt to form an ionic crosslink, or condensed with a diol, diamine, or other symmetrically or asymmetrically di-substituted reagent to form a covalent crosslink.

Some embodiments of the invention are directed to a method for the preparation of the MC1R-ligands comprising a functional group that can undergo a click reaction. The method involves preparation of a peptide sequence comprising a 4-propynyl amide at either the C terminal or, alternately, the N terminal end of the peptide. The peptide can be prepared using a Rink Amide Tentagel resin (0.23 mmol/g) using a Fmoc/tBu synthetic strategy and standard activations. The protected peptide is selectively deprotected with cleavage of the Aloc group, and subsequently condensed with a click reagent containing compound, for example a 5-hexynoic acid, to form the 5-hexynyl amide group, as the site for surface attachment of the MC1R-ligand. The remainder of the protection groups and the cleavage from the resin can be carried out by addition of a TFA scavenger cocktail.

Some embodiments of the invention are directed to the functionalization of a surface with a MC1R peptide ligand comprising a functional group for a click reaction and a surface comprising the complementary functional group. In an embodiment of the invention, an MC1R peptide ligand comprises an alkyne functional group at an amino acid residue at the C terminal end, or alternately at the N terminal end, is added to functional group of a surface of an in vivo stable micelle. In cases where the surface is the surface of a micelle, a MC1R peptide ligand micelle complex can be formed.

Some embodiments of the invention are directed to the delivery of drugs, contrast agents, or other agents attached to the MC1R peptide ligand or contained within a particle or micelle that is attached to the MC1R peptide ligand, to a patient. The micelle can be an in-vivo stable micelle that can de-crosslink at a low pH.

As used herein, the terms "administering" or "administer" is defined as the introduction of a substance (MC1R peptide ligand or complex) into cells in vitro or into the body of an individual in vivo and includes topical, dermal, oral, nasal, ocular, rectal, vaginal and parenteral routes of administration. The administration may be by any suitable method known in the medicinal arts, including, but not limited to, subcutaneous, intramuscular, intravenous, intraperitoneal, intradermal via the nasal, ocular or oral mucosa, oral, parenteral (e.g. intramuscular, subcutaneous, intraperitoneal or intravenous), or topical administration. The MC1R peptide ligand or complex may be administered individually or in combination with other agents via any route of administration. For example, the MC1R peptide ligand or complex can be administered by direct injection into a tumor or at a site remote from the tumor.

The MC1R peptide ligand or complex can be administered to treat a disorder, such as skin cancer. As used herein, the terms "treat" or "treatment" refer to both therapeutic treatment and prophylactic or preventative measures, wherein the object is to prevent or slow down (lessen) an undesired physiological change or disorder, such as the development or spread of cancer or other proliferation disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. For example, treatment with a peptide of the invention may include reduction of undesirable cell proliferation, and/or induction of apoptosis and cytotoxicity. "Treatment" can also mean prolonging survival as compared to expected survival if not receiving treatment. Those in need of treatment include those already with the condition or disorder as well as those prone to have the condition or disorder or those in which the condition or disorder is to be prevented or onset delayed. Optionally, the patient may be identified (e.g., diagnosed) as one suffering from the disease or condition (e.g., cancer) prior to administration of the peptide of the invention. By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, side effects associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition. As such, treatment includes both curing and managing a disease condition.

As defined herein, the terms "therapeutically effective amount" means the amount of a compound that, when administered to a mammal for treating a condition, is sufficient to effect such treatment for the condition. The "therapeutically effective amount" will vary depending on the compound, the condition and its severity and body factors such as age, weight, etc., of the mammal to be treated. For instance, a "therapeutically effective amount" of the MC1R peptide ligand or complex of the invention or other agent (e.g., a drug) is effective to treat a disease or disorder in a mammal. In the case of cancer or other proliferation disorder, the therapeutically effective amount of the agent may reduce (i.e., slow to some extent and preferably stop) unwanted cellular proliferation; reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve, to some extent, one or more of the symptoms associated with the cancer. To the extent the administered MC1R peptide ligand or complex prevents growth of and/or kills existing cancer cells, it may be cytostatic and/or cytotoxic. For cancer therapy, efficacy can, for example, be measured by assessing the time to disease progression (TTP) and/or determining the response rate (RR).

Methods described herein may be equivalently represented in a Swiss-type format. As a non-limiting example, "a method for treating a disease Y using compound X" may have a Swiss-type equivalent of "the use of compound X in curing disease Y". It is to be understood that other Swiss-type formats may be acceptable.

The present invention provides an MCIR peptide ligand for use in any application in which the administration of the MCIR peptide ligand to a subject is desired. The terms "subject", "individual", or "patient" as used herein refer to any human or non-human animal, including mammals, to whom treatment with a composition according to the present invention is provided. Generally such subjects are "mammals" or "mammalian," where these terms are used broadly to describe organisms which are within the class mammalia. *Mammalian* species that benefit from the disclosed methods of treatment include, and are not limited to, apes, chimpanzees, orangutans, humans, monkeys; domesticated animals (e.g., pets) such as dogs, cats, guinea pigs, hamsters, rabbits, rats, mice, and ferrets; and domesticated farm animals such as cows, horses, swine, and sheep.

The methods of the present invention can be advantageously combined with at least one additional diagnostic and/or treatment method, including but not limited to, chemotherapy, radiation therapy, surgery, immunotherapy or any other therapy known to those of skill in the art for the treatment and management of a cancer.

While MC1R peptide ligands of the invention can be administered to cells in vitro and in vivo as isolated agents, it is preferred to administer these MC1R peptide ligands as part of a pharmaceutical composition. The subject invention thus further provides compositions comprising a peptide of the invention in association with at least one pharmaceutically acceptable carrier. The pharmaceutical composition can be adapted for various routes of administration, such as enteral, parenteral, intravenous, intramuscular, topical, subcutaneous, intratumoral, and so forth. Administration can be continuous or at distinct intervals, as can be determined by a person of ordinary skill in the art.

The MC1R peptide ligands of the invention can be formulated according to known methods for preparing pharmaceutically useful compositions. Formulations are described in a number of sources which are well known and readily available to those skilled in the art. For example, Remington's Pharmaceutical Science (Martin, E. W., 1995, Easton Pa., Mack Publishing Company, 19.sup.th ed.) describes formulations which can be used in connection with the subject invention. Formulations suitable for administration include, for example, aqueous sterile injection solutions, which may contain antioxidants, buffers, bacteriostats, and solutes that render the formulation isotonic with the blood of the intended recipient; and aqueous and nonaqueous sterile suspensions which may include suspending agents and thickening agents.

The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the compositions of the subject invention can include other agents conventional in the art having regard to the type of formulation in question.

Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts of compounds may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The active agent (MC1R peptide ligands) may also be administered intravenously or intraperitoneally by infusion or injection. Solutions of the active agent can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the compounds of the invention which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants.

MC1R peptide ligands of the invention may be administered locally at the desired anatomical site, such as a tumor site, or remote from the desired state, or systemically. Sterile injectable solutions are prepared by incorporating the MC1R peptide ligands of the invention in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the agents may be applied in pure-form, i.e., when they are liquids. However, it will generally be desirable to administer them topically to the skin as formulations, in combination with an acceptable carrier, which may be a solid or a liquid. The preferred administration form is topically, and includes gels, creams, ointments, sprays, lotions, salves, sticks, soaps, powders, films, aerosols, drops, foams, pastes, solutions, emulsions, suspensions, dispersions e.g. non-ionic vesicle dispersions, milks and any other conventional pharmaceutical forms in the art. The use of solutions, suspensions, gels and emulsions are preferred, e.g. the active ingredient may be carried in water, a gas, a water-based liquid, an oil, a gel, an emulsion, an oil-in water or water-in-oil emulsions a dispersion or a mixture thereof.

In some embodiments, the present invention features a pharmaceutical composition that may be used for the topical or transdermal administration of the MC1R peptide ligand. As used throughout this specification, the term 'transdermal', means in the broadest sense through the skin. In some embodiments, topical or transdermal formulations may comprise the pharmaceutical composition described herein. As used herein, the term 'topical formulation' refers to a formulation that may be applied to body coverings or surfaces such as skin, bodily outgrowths such as hair and nails and surfaces such as mucosal membranes. Topical formulations may, for example, be used to confer therapeutic benefit to a patient or cosmetic benefits to a consumer. Topical formulations can be used for both topical and transdermal administration of substances. The term 'topical administration' is used in its conventional sense to mean delivery of a substance, such as the MC1R peptide ligand, to the skin or a localized region of the body, advantageous for, for example, the treatment of various skin disorders. The term 'transdermal administration' is used to mean administration through the skin. Transdermal administration is often applied where systemic delivery of the MC1R peptide ligand is desired, although it may also be useful for delivering the MC1R peptide ligand to tissues underlying the skin with minimal systemic absorption.

As used herein, "pharmaceutically acceptable carrier/excipients", means one or more substantially non-irritating compatible filler diluents which are suitable for topical application to the skin of a mammal, i.e. human. The term "compatible", as used herein, means that the components of the carrier must be capable of being comingled with the compositions, and with each other, in a manner such that there is no interaction which would substantially reduce the efficacy of the composition during use. Pharmaceutically-acceptable carriers/excipients must, of course, be of sufficiently high purity and sufficiently low toxicity to render them suitable for topical administration to the mammal. The present pharmaceutical composition may include one or more pharmaceutically acceptable carriers/excipients. Suitable carriers/excipients that may be used are known in the art and include, but are not limited to, solubilizers such as C2 to C8 straight and branched chain alcohols, diols and triols, moisturizers and humectants such as glycerine, amino acids and amino acid derivatives, polyaminoacids and derivatives, pyrrolidone carboxylic acids and its salts and derivatives, surfactants such as sodium laureth sulfate, sorbitan monolaurate, emulsifiers such as cetyl alcohol, stearyl alcohol, thickeners such as methyl cellulose, ethyl cellulose, hydroxymethylcellulose, hydroxypropylcellulose, polyvinylpyrollidone, polyvinyl alcohol and acrylic polymers, water, oils, fats, waxes, synthetic polymers, perfumes, dyes, and preservatives. Other examples of suitable excipients, such as binders and fillers are listed in Handbook of Pharmaceutical Excipients, $7^{th}$ Edition, Ed. Raymond C. Rowe, Pharmaceutical Press, 2012.

The MC1R peptide ligand of the pharmaceutical composition may be incorporated, optionally together with other active substances as a combined preparation, with one or more conventional carriers, diluents and/or excipients, to produce conventional galenic preparations such as tablets, pills, powders, lozenges, sachets, cachets, elixirs, suspensions (as injection or infusion fluids), emulsions, solutions, syrups, aerosols (as a solid or in a liquid medium), ointments, soft and hard gelatin capsules, suppositories, sterile injectable solutions, sterile packaged powders, and the like.

The pharmaceutical compositions may be formulated so as to provide quick, sustained or delayed release of the MC1R peptide ligand after administration to the body by employing techniques well known in the art. The pharmaceutical composition may be in any appropriate dosage form to allow delivery or for targeting particular cells or tissues, e.g. as an emulsion or in liposomes, niosomes, microspheres, nanoparticles or the like with which the active ingredient may be absorbed, adsorbed, incorporated or bound. This can effectively convert the product to an insoluble form. These particulate forms may overcome both stability (e.g. degradation) and delivery problems. These particles may carry appropriate surface molecules to improve circulation time (e.g. serum components, surfactants, polyoxamine908, PEG etc.) or moieties for site-specific targeting, such as ligands to particular cell borne receptors.

Ointments, gels and creams may, for example, be formulated with an aqueous or oily base with the addition of suitable thickening and/or gelling agents. Lotions may be formulated with an aqueous or oily base and will, in general, also contain one or more emulsifying, dispersing, suspending, thickening or coloring agents. Powders may be formed with the aid of any suitable powder base. Drops and solutions may be formulated with an aqueous or nonaqueous base also comprising one or more dispersing, solubilizing or suspending agents. Aerosol sprays are delivered from pressurized packs, with the use of a suitable propellant.

The concentration of active ingredient (MC1R peptide ligand) in compositions of the invention, depends upon the nature of the compound used, the mode of administration, the course of treatment, the age and weight of the patient, the cosmetic or medical indication, the body or body area to be treated and may be varied or adjusted according to choice. Generally however, concentration ranges for the compound described herein is 0.0005, 0.001 or 0.01 to 25%, e.g. 0.01 to 10% or 0.01-20%, such as 1-5% (w/w of the final preparation for administration, particularly for topical administration). Said concentrations are determined by reference to the amount of the compound itself and thus appropriate allowances should be made to take into account the purity of the composition. Effective single doses may lie in the range of from 1-100 mg/day, preferably 2-10 mg/day, depending on the animal being treated, taken as a single dose. Useful dosages of the pharmaceutical compositions of the present invention can be determined by comparing their in vitro activity, and in vivo activity in animal models. Methods for the extrapolation of effective dosages in mice, and other animals, to humans are known in the art; for example, see U.S. Pat. No. 4,938,949.

The agents of the subject invention can be applied topically to a subject's skin to reduce the size (and may include complete removal) of malignant or benign growths. The MC1R peptide ligands of the invention can be applied directly to the growth. For example, the MC1R peptide ligand may be applied to the growth in a formulation such as an ointment, cream, lotion, solution, tincture, or the like. Drug delivery systems for delivery of pharmacological substances to dermal lesions can also be used, such as that described in U.S. Pat. No. 5,167,649 (Zook).

Useful solid carriers include finely divided solids such as talc, clay, microcrystalline cellulose, silica, alumina and the like. Useful liquid carriers include water, alcohols or glycols or water-alcohol/glycol blends, in which the peptide can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, xanthan gum, modified celluloses or modified mineral materials can also be employed with liquid carriers to form spreadable pastes, gels, ointments, soaps, and the like, for application directly to the skin of the user. Examples of useful dermatological compositions which can be used to deliver the peptides to the skin are disclosed in Jacquet et al. (U.S. Pat. No. 4,608,392), Geria (U.S. Pat. No. 4,992,478), Smith et al. (U.S. Pat. No. 4,559,157) and Woltzman (U.S. Pat. No. 4,820,508).

In some embodiments, patch preparations find use in applications of topically delivering the pharmaceutical composition to a subject, particularly the skin of a subject. In practicing the invention, the patch may be administered to any convenient topical site. Topical sites of interest include, but are not limited to: arms, leg, torso, head, etc. The surface area that is covered by the topical patch preparation following application must be sufficient to provide for the desired amount of administration of the MC1R peptide ligand, for instance, from about 1 to 200 $cm^2$, and in many embodiments from about 10 to 180 $cm^2$, usually from about 100 to 150 $cm^2$.

In representative embodiments, the period of time required to deliver the desired amount of the MC1R peptide ligand is generally not exceeding about 48 hours, usually not exceeding about 24 hours. However, the period of time during which the preparation is maintained at the application site is at least about 30 minutes, usually at least about 1 hour.

In practicing the subject methods, the topical formulations or patches having the pharmaceutical composition may be applied a single time or a plurality of times over a given time period, e.g., the course of the disease condition being treated, where the dosing schedule when the pharmaceutical composition is administered over a given time period may be multiple times per day (i.e. three times per day), daily, weekly, biweekly, monthly, etc.

As used herein a "photoprotective composition" refers to a composition which is suitable for administration to an individual which provides protection against light irradiation, particularly of ultraviolet and visible light in the wavelengths of about 200-800 nm, preferably by stimulating melanin synthesis, such as eumelanin. Preferably, the MC1R peptide ligand of the photoprotective composition is capable of achieving protection in these wavelength ranges.

As used herein, "irradiation" refers to direct or indirect irradiation from one or more natural or synthetic light sources, particularly from the sun, i.e. solar radiation. Preferably said radiation is of light in the range 200-800 nm. The "effects" of irradiation may be damaging effects including burns, erythema, premature aging and wrinkling of the skin, and skin cancer, including benign and malignant tumors.

The method of treatment or prevention according to the invention may advantageously be combined with administration of one or more active ingredients which are effective in treating or preventing the effects of irradiation. Preferably such active ingredients include antioxidants, vitamins and other ingredients conventionally employed in the art.

Alternatively, the compositions may be provided in a form adapted for oral or parenteral administration. Pharmaceutical forms include plain or coated tablets, capsules, suspensions and solutions containing the MC1R peptide ligand optionally together with one or more inert carriers and/or diluents, e.g. with corn starch, lactose, sucrose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fatty substances such as hard fat or suitable mixtures thereof.

Patients in need of treatment and/or diagnosis using the compositions and methods of the present invention can be identified using standard techniques known to those in the medical or veterinary professions, as appropriate.

As used herein, the term "growth inhibitory amount" of the MC1R peptide ligand or complex of the invention refers to an amount which inhibits growth or proliferation of a target cell, such as a tumor cell, either in vitro or in vivo, irrespective of the mechanism by which cell growth is inhibited (e.g., by cytostatic properties, cytotoxic properties, etc.). In a preferred embodiment, the growth inhibitory amount inhibits (i.e., slows to some extent and preferably stops) proliferation or growth of the target cell in vivo or in cell culture by greater than about 20%, preferably greater than about 50%, most preferably greater than about 75% (e.g., from about 75% to about 100%).

The terms "cell" and "cells" are used interchangeably herein and are intended to include either a single cell or a plurality of cells, in vitro or in vivo, unless otherwise specified.

As used herein, the term "tumor" refers to all neoplastic cell growth and proliferation, whether malignant or benign, and all pre-cancerous and cancerous cells and tissues. For example, a particular cancer may be characterized by a solid tumor mass or a non-solid tumor. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture, or weight of the tissue. However, some primary tumors are not palpable and can be detected only through medical imaging techniques such as X-rays (e.g., mammography), or by needle aspirations. The use of these latter techniques is more common in early detection. Molecular and phenotypic analysis of cancer cells within a tissue will usually confirm if the cancer is endogenous to the tissue or if the lesion is due to metastasis from another site. Depending upon the type of agent (payload) utilized, the compositions of the invention may be capable of inducing apoptosis in tumor cells and reducing tumor cell growth. The compositions of the invention can be administered locally at the site of a tumor (e.g., by direct injection) or remotely. Depending upon the payload, the compositions of the invention can induce cell death in circulating tumor cells (CTC) in a subject, e.g., by administering the compositions intravenously. Furthermore, depending upon payload, the compositions of the invention can prevent or reduce onset of metastasis to other tissues. Furthermore, in cases in which the payload is a detectable moiety, such as a contrast agent, the compositions of the invention can be used to detect metastasis to other tissues and potentially avoid the need for nodal biopsy.

In some embodiments, an agent is coupled to the MC1R peptide ligand or incorporated within the micelle of the complex. In some embodiments, the agent is an anti-cancer agent, such as a chemotherapeutic agent, biologic, etc. having anti-cancer activity. As used herein, the term "payload" refers to agents and moieties linked to the MC1R peptide ligand or residing within the inner core of the MC1R peptide ligand-micelle complex. The payload may be any desired agent or moiety that is capable of being directly or indirectly linked to the MC1R peptide ligand or incorporated within the micelle. Examples of payloads include, but are not limited to, molecules such as contrast agents (e.g., detectable substances such as dyes), biologically active agents, such as biologics, anti-cancer agents such as chemotherapeutic agents, or other drugs. The terms "payload", "agent", and "moiety" are used interchangeably herein.

As used herein, the term "elastic vesicle" refers to a highly flexible and deformable moiety, known as a Transferosome®. These elastic vesicles were first introduced by Gregor Cevc. They are a means of transporting biogenic molecules into the body via transdermal delivery. The elastic vesicle is composed of liposomes and a biocompatible surfactant to form a lipid bilayer. In some embodiments, the liposomes form a lipid bilayer. In some embodiments, the lipid bilayer comprises lipids from an ethanolic soybean phosphatidylcholine, a soya phosphatidylcholine, a dipalmitoyl phosphatidylcholine, or a distearoyl phosphatidylcholine. In some embodiments, the surfactant is a sodium cholate or a sodium deoxycholate The following is a non-limiting example of preparing the elastic vesicle (Cevc et al., Biochimica et Biophysica Acta (1998)). Liposomes comprising soybean phosphatidylcholine (SPC) was dried under vacuum (10 Pa) overnight to form a lipid film. The lipid film was hydrated with triethanolamine-HCL buffer (pH=6.5) to prepare a 10% lipid suspension and then sonicated for 60 min at 4° C. until the desired vesicle radius is achieved. The ethanolic SPC solution was mixed with sodium cholate to produce a suspension containing 8.7 wt % SPC, 1.3 wt % cholate and approximately 8.5 vol % ethanol. The suspension was mixed with triethanolamine-HCL buffer (pH=6.5) to yield a 10 wt % lipid concentration suspension. The latter suspension was sonicated, frozen and thawed about two to three times and then processed by ultrasonication or intermediate-pressure homogenization until the desired size was achieved. The final vesicle suspension was sterilized by filtration. The MSH peptide ligand may be added to the elastic vesicle during preparation or after preparation of the elastic vesicle. For example, the MSH peptide ligand may be linked to or inserted into the elastic vesicle.

The practice of the present invention can employ, unless otherwise indicated, conventional techniques of molecular biology, microbiology, recombinant DNA technology, electrophysiology, and pharmacology that are within the skill of the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover Ed. 1985); Perbal, B., A Practical Guide to Molecular Cloning (1984); the series, Methods In Enzymology (S. Colowick and N. Kaplan Eds., Academic Press, Inc.); Transcription and Translation (Hames et al. Eds. 1984); Gene Transfer Vectors For Mammalian Cells (J. H. Miller et al. Eds. (1987) Cold Spring Harbor Laboratory, Cold Spring Harbor, N.Y.); Scopes, Protein Purification Principles and Practice (2nd ed., Springer-Verlag); and PCR: A Practical Approach (McPherson et al. Eds. (1991) IRL Press)), each of which are incorporated herein by reference in their entirety.

As used in this specification, the singular forms "a", "an", and "the" include plural reference unless the context clearly dictates otherwise. Thus, for example, a reference to "a cell" includes one or more cells. A reference to "a peptide" includes one or more such peptide, and so forth. As used herein, the terms "those defined above" and "those defined herein" when referring to a variable incorporates by reference the broad definition of the variable as well as any narrow and/or preferred, more preferred and most preferred definitions, if any.

Figure 2:
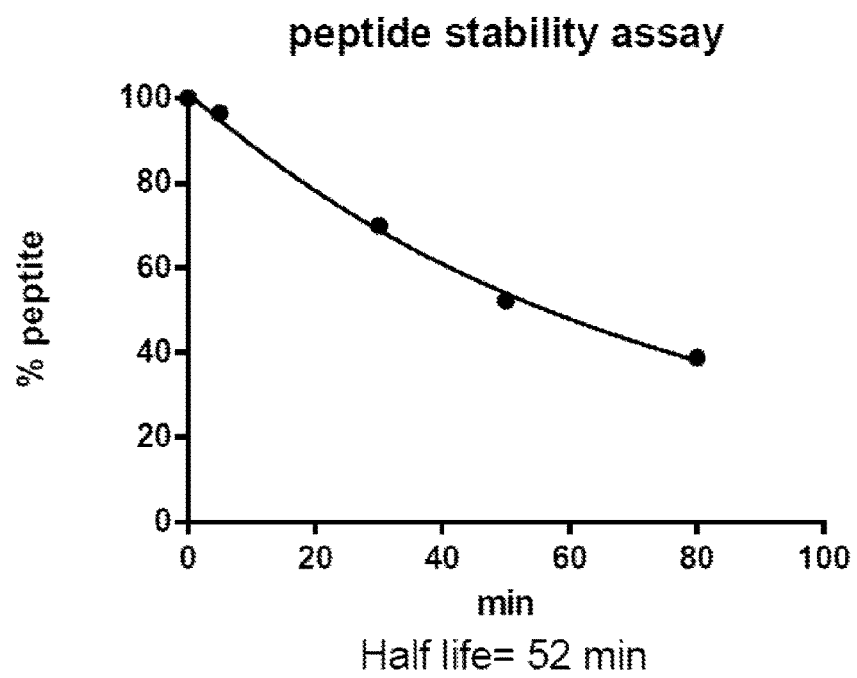
FIG. 2 shows a peptide stability assay of the hMC1R selective γ-MSH analogue (SEQ ID NO. 11) according to an embodiment of the present invention. The embodiment in FIG. 2 has a half-life of 52 minutes.
Figure 3:
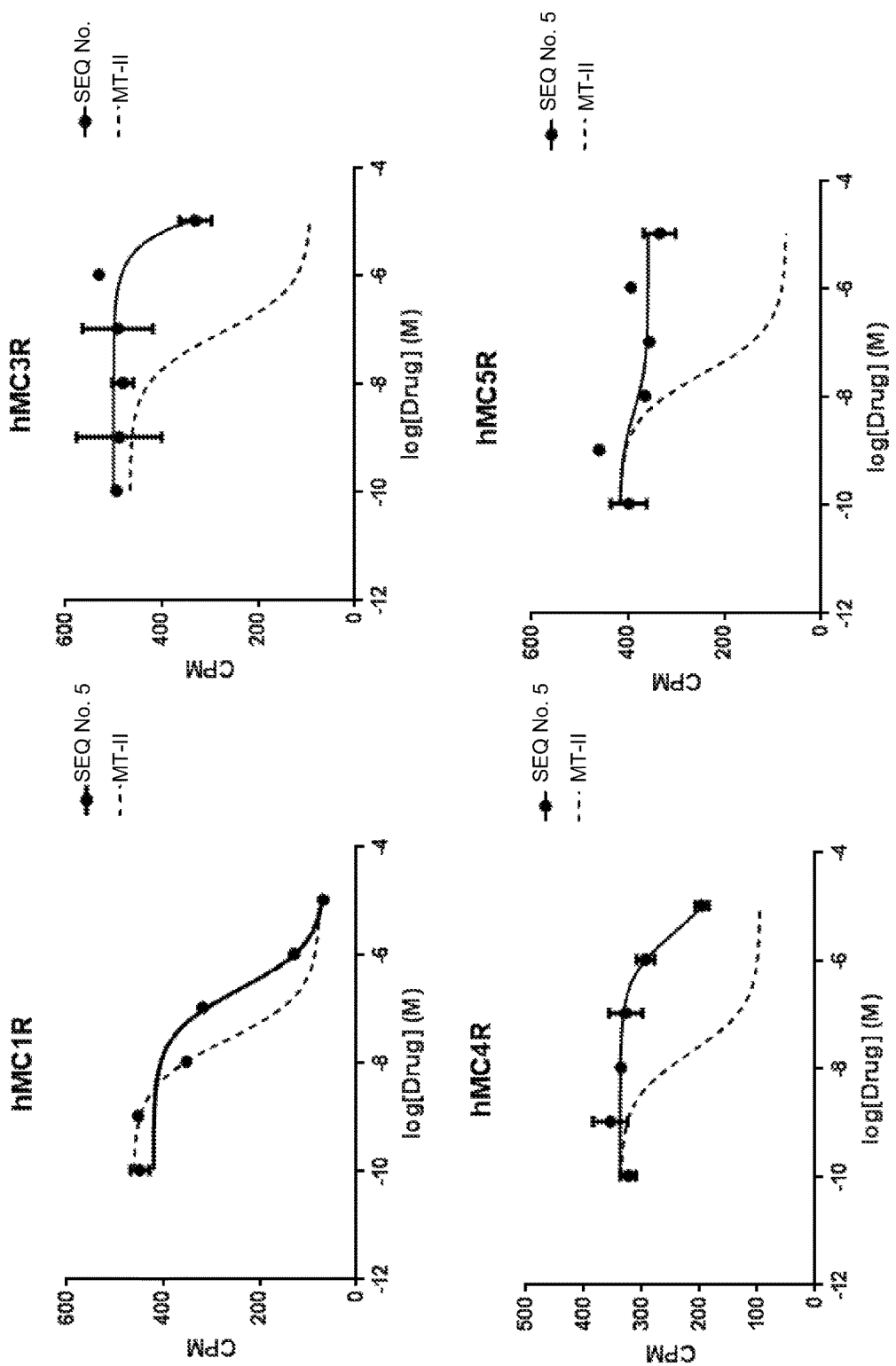
FIG. 3 shows a binding assay of an exemplary hMC1R selective γ-MSH analogue (SEQ ID NO. 5) towards the subtypes of human melanocortin receptors. MTII is a universal agonist for all subtype of hMCRs. The MTII data is also shown in the same assay of SEQ ID NO. 5 to prove that the assay system of the present invention is working correctly.

Referring now to FIG. 1-3, the present invention features a derivative of γ-MSH using natural amino acids that render it more MC1R selective and more stable and bioavailable. In some embodiments, the present invention features a modified melanocortin 1 receptor (MC1R) peptide ligand comprising naturally occurring amino acids. Preferably, the MC1R peptide ligand is be a derivative of γ-melanocyte stimulation hormone (γ-MSH). However, the MC1R peptide ligand can be a derivative of any melanocyte stimulation hormone.

In one embodiment, the MC1R peptide ligand comprising naturally occurring amino acids may be according to SEQ ID NO: 1:

```
                                                       (SEQ ID NO: 1)
H-Tyr¹-Val²-Waa³-Gly⁴-Xaa⁵-Phe⁶-Yaa⁷-Zaa⁸-

Asp⁹-Arg¹⁰-Phe¹¹-Gly¹²-R1
``` wherein Waa is a Met, Ile, or Leu; Xaa is a His or Pro; Yaa is an Arg or Leu; and Zaa is a Phe or Trp, and R1 of the C-terminal is —NH$_2$, or —OH. For instance, Waa is Leu, Xaa is His, Yaa is Leu, Zaa is Phe, and R1 is —NH$_2$.

In preferred embodiments, there is a caveat on that Waa is not Met, Xaa is not His, Yaa is not Arg, Zaa is not Trp, and R1 is not —OH simultaneously, i.e. SEQ ID NO. 1 is not H-Tyr¹-Val²-Met³-Gly⁴-His⁵-Phe⁶-Arg⁷-Trp⁸-Asp⁹-Arg¹⁰-Phe¹¹-Gly¹²-OH (SEQ ID NO. 13).

According to another embodiment, the MC1R peptide ligand comprising naturally occurring amino acids is selected from a group consisting of:

```
                                                       (SEQ ID NO: 2)
H-Tyr-Val-Leu-Gly-Pro-Phe-Arg-Trp-Asp-Arg-Phe-Gly-

NH₂;

(SEQ ID NO: 3)
H-Tyr-Val-Leu-Gly-Pro-Phe-Arg-Phe-Asp-Arg-Phe-Gly-

NH₂;

(SEQ ID NO: 4)
H-Tyr-Val-Leu-Gly-His-Phe-Leu-Trp-Asp-Arg-Phe-Gly-

NH₂;

(SEQ ID NO: 5)
H-Tyr-Val-Leu-Gly-His-Phe-Leu-Phe-Asp-Arg-Phe-Gly-

NH₂;

(SEQ ID NO: 6)
H-Tyr-Val-Leu-Gly-Pro-Phe-Leu-Trp-Asp-Arg-Phe-Gly-

NH₂;

(SEQ ID NO: 7)
H-Tyr-Val-Leu-Gly-Pro-Phe-Leu-Phe-Asp-Arg-Phe-Gly-

NH₂;

(SEQ ID NO: 8)
H-Tyr-Val-Leu-Gly-His-Phe-Arg-Trp-Asp-Arg-Phe-

Gly-OH (SEQ ID NO: 9)
H-Tyr-Val-Leu-Gly-His-Phe-Arg-Trp-Asp-Arg-Phe-Gly-

NH₂;
and (SEQ ID NO: 10)
H-Tyr-Val-Met-Gly-Pro-Phe-Arg-Trp-Asp-Arg-Phe-Gly-

NH₂.
```

In yet another embodiment, the present invention features an MC1R peptide ligand comprising naturally occurring amino acids according to SEQ ID NO. 5:

```
                                                       (SEQ ID NO: 5)
H-Tyr-Val-Leu-Gly-His-Phe-Leu-Phe-Asp-Arg-Phe-

Gly-NH₂
```

The MC1R peptide ligand according to SEQ ID NO. 5 has been surprisingly discovered to be highly selective for MC1R.

In some embodiments, the MC1R peptide ligand described herein is an agonist of MC1R and is capable of stimulating melanin production. Preferably, the MC1R peptide ligand is selective for MC1R. For example, wherein the MC1R peptide ligand is at least twice as selective for MC1R than MC3R, MC4R, or MC5R. In other embodiments, the MC1R peptide ligand is at least 3, 4, or 5 times more selective for MC1R than for the other melanocortin receptors.

According to one embodiment, the present invention provides for a pharmaceutical composition for preventing skin cancer. The composition may comprise a melanocortin 1 receptor (MC1R) peptide ligand, together with a pharmaceutically acceptable carrier. Preferably, the MC1R peptide ligand comprises naturally occurring amino acids. The MC1R peptide ligand may be according to SEQ ID NO. 1:

```
                                                       (SEQ ID NO: 1)
H-Tyr¹-Val²-Waa³-Gly⁴-Xaa⁵-Phe⁶-Yaa⁷-Zaa⁸-

Asp⁹-Arg¹⁰-Phe¹¹-Gly¹²-R1
``` wherein Waa is a Met, Ile, or Leu; Xaa is a His or Pro; Yaa is an Arg or Leu; and Zaa is a Phe or Trp; and R1 of the C-terminal is —NH$_2$, or —OH. Preferably, Waa is not Met, Xaa is not His, Yaa is not Arg, Zaa is not Trp, and R1 is not —OH simultaneously. In preferred embodiments, the MC1R peptide ligand is selective for MC1R and is an agonist of MC1R, such that the MC1R peptide ligand is capable of stimulating melanin production, thereby preventing skin cancer.

According to another embodiment, the present invention provides for a pharmaceutical composition for stimulating melanin production. The composition can comprise a melanocortin 1 receptor (MC1R) peptide ligand, together with a pharmaceutically acceptable carrier. Preferably, the MC1R peptide ligand comprises naturally occurring amino acids. The MC1R peptide ligand may be according to SEQ ID NO. 1:

```
                                                       (SEQ ID NO: 1)
H-Tyr¹-Val²-Waa³-Gly⁴-Xaa⁵-Phe⁶-Yaa⁷-Zaa⁸-

Asp⁹-Arg¹⁰-Phe¹¹-Gly¹²-R1
``` wherein Waa is a Met, Ile, or Leu; Xaa is a His or Pro; Yaa is an Arg or Leu; and Zaa is a Phe or Trp; and R1 of the C-terminal is —NH$_2$, or —OH. Preferably, Waa is not Met, Xaa is not His, Yaa is not Arg, Zaa is not Trp, and R1 is not —OH simultaneously. In preferred embodiments, the MC1R peptide ligand is selective for MC1R and is an agonist of MC1R, such that the MC1R peptide ligand is capable of stimulating melanin production.

In preferred embodiments, the pharmaceutical composition described herein is administered topically for topical or transdermal delivery of the MC1R peptide ligand through skin. In one embodiment, the pharmaceutical composition can be in a form of a gel, a hydrogel, a water-in-oil emulsion, an oil-in-water emulsion, a cream, a lotion, an ointment, a spray, a foam, a multi-emulsion, or a liposome.

In another embodiment, the pharmaceutical composition is in a form of a patch. For example, the patch may comprise an impenetrable outer layer and a permeable inner layer, in which the outer layer and the inner layer form a reservoir for storing the pharmaceutical composition. When the patch is applied on a skin of mammal, the pharmaceutical composition can permeate through the inner layer and the MC1R peptide ligand can pass through the skin. The aforementioned patch is but one non-limiting example of a patch preparation, and it understood that other configurations of patches, namely any patch capable of being applied to the skin and delivering the pharmaceutical composition, may be used in accordance with the present invention.

In some embodiments, the MC1R peptide ligand is present in an amount ranging from about 0.001-50 wt % of the pharmaceutical composition. In exemplary embodiments, the amount of MC1R peptide ligand in the pharmaceutical composition can range from about 0.001-5 wt %, or 5-15 wt %, or 10-25 wt %, or 20-35 wt %, or 30-45 wt %, or 40-50 wt %.

In one embodiment, the pharmaceutical composition described herein comprises the MC1R peptide ligand selected from a group consisting of:

```
                                                 (SEQ ID NO: 2)
H-Tyr-Val-Leu-Gly-Pro-Phe-Arg-Trp-Asp-Arg-Phe-Gly-
NH₂;
                                                 (SEQ ID NO: 3)
H-Tyr-Val-Leu-Gly-Pro-Phe-Arg-Phe-Asp-Arg-Phe-Gly-
NH₂;
                                                 (SEQ ID NO: 4)
H-Tyr-Val-Leu-Gly-His-Phe-Leu-Trp-Asp-Arg-Phe-Gly-
NH₂;
                                                 (SEQ ID NO: 5)
H-Tyr-Val-Leu-Gly-His-Phe-Leu-Phe-Asp-Arg-Phe-Gly-
NH₂;
                                                 (SEQ ID NO: 6)
H-Tyr-Val-Leu-Gly-Pro-Phe-Leu-Trp-Asp-Arg-Phe-Gly-
NH₂;
                                                 (SEQ ID NO: 7)
H-Tyr-Val-Leu-Gly-Pro-Phe-Leu-Phe-Asp-Arg-Phe-Gly-
NH₂;
                                                 (SEQ ID NO: 8)
H-Tyr-Val-Leu-Gly-His-Phe-Arg-Trp-Asp-Arg-Phe-
Gly-OH
                                                 (SEQ ID NO: 9)
H-Tyr-Val-Leu-Gly-His-Phe-Arg-Trp-Asp-Arg-Phe-Gly-
NH₂;
and
                                                 (SEQ ID NO: 10)
H-Tyr-Val-Met-Gly-Pro-Phe-Arg-Trp-Asp-Arg-Phe-Gly-
NH₂.
```

In another embodiment, the pharmaceutical composition described herein comprises the MC1R peptide ligand according to SEQ ID NO: 5:

```
                                                 (SEQ ID NO: 5)
H-Tyr-Val-Leu-Gly-His-Phe-Leu-Phe-Asp-Arg-Phe-Gly-
NH₂.
```

According to yet another embodiment, the present invention features a method of preventing skin cancer in a mammal. The method may comprise administering to the mammal a therapeutically effective amount of a melanocortin 1 receptor (MC1R) peptide ligand comprising naturally occurring amino acids. In a preferred embodiment, the MC1R peptide ligand is according to SEQ ID NO. 1:

$$\text{H-Tyr}^1\text{-Val}^2\text{-Waa}^3\text{-Gly}^4\text{-Xaa}^5\text{-Phe}^6\text{-Yaa}^7\text{-Zaa}^8\text{-Asp}^9\text{-Arg}^{10}\text{-Phe}^{11}\text{-Gly}^{12}\text{-R1} \quad (\text{SEQ ID NO: 1})$$

wherein Waa is a Met, Ile, or Leu; Xaa is a His or Pro; Yaa is an Arg or Leu; Zaa is a Phe or Trp; and R1 of the C-terminal is —NH₂, or —OH. The MC1R peptide ligand of Formaula 1 has a caveat that Waa is not Met, Xaa is not His, Yaa is not Arg, Zaa is not Trp, and R1 is not —OH simultaneously. Without wishing to limit the invention to a particular theory or mechanism, the MC1R peptide ligand is selective for and is an agonist of MC1R; hence, the MC1R peptide ligand is capable of stimulating melanin production, thereby preventing skin cancer.

According to a further embodiment, the present invention features a method of stimulating melanin production in a mammal. The method may comprise administering to the mammal a melanocortin 1 receptor (MC1R) peptide ligand in an amount sufficient for stimulation. The MC1R peptide ligand can comprise naturally occurring amino acids, such that the MC1R peptide ligand is according to SEQ ID NO. 1:

$$\text{H-Tyr}^1\text{-Val}^2\text{-Waa}^3\text{-Gly}^4\text{-Xaa}^5\text{-Phe}^6\text{-Yaa}^7\text{-Zaa}^8\text{-Asp}^9\text{-Arg}^{10}\text{-Phe}^{11}\text{-Gly}^{12}\text{-R1} \quad (\text{SEQ ID NO: 1})$$

wherein Waa is a Met, Ile, or Leu; Xaa is a His or Pro; Yaa is an Arg or Leu; Zaa is a Phe or Trp; and R1 of the C-terminal is —NH₂, or —OH. However, there is a caveat that Waa is not Met, Xaa is not His, Yaa is not Arg, Zaa is not Trp, and R1 is not —OH simultaneously. In preferred embodiments, the MC1R peptide ligand is selective for and is an agonist of MC1R, therefore the MC1R peptide ligand is capable of stimulating melanin production.

In still a further embodiment, the present invention features a method of treating or protecting against the effects of UV radiation in a mammal. The method may comprises topically administering to said mammal a photoprotective composition comprising a melanocortin 1 receptor (MC1R) peptide ligand, and one or more pharmaceutically acceptable excipients and/or diluents. The MC1R peptide ligand may comprise naturally occurring amino acids. In preferred embodiments, the MC1R peptide ligand is according to SEQ ID NO. 1:

$$\text{H-Tyr}^1\text{-Val}^2\text{-Waa}^3\text{-Gly}^4\text{-Xaa}^5\text{-Phe}^6\text{-Yaa}^7\text{-Zaa}^8\text{-Asp}^9\text{-Arg}^{10}\text{-Phe}^{11}\text{-Gly}^{12}\text{-R1} \quad (\text{SEQ ID NO: 1})$$

wherein Waa is a Met, Ile, or Leu; Xaa is a His or Pro; Yaa is an Arg or Leu; Zaa is a Phe or Trp; and R1 of the C-terminal is —NH₂, or —OH; with the caveat that Waa is not Met, Xaa is not His, Yaa is not Arg, Zaa is not Trp, and R1 is not —OH simultaneously. Without wishing to limit the invention to a particular theory or mechanism, the MC1R peptide ligand is selective for and is an agonist of MC1R; hence, the MC1R peptide ligand is capable of stimulating melanin production, thereby treating or protecting the mammal against the effects of UV radiation.

In preferred embodiments, the MC1R peptide ligand of the methods described herein is administered topically for topical or transdermal delivery of the MC1R peptide ligand through skin. In some embodiments, the amount of MC1R peptide ligand being administered can range from about from about 0.001 to 50 wt % of the final preparation for administration. For example, the amount of MC1R peptide ligand in the final preparation for administration can range from about 0.001-5 wt %, or 5-15 wt %, or 10-25 wt %, or 20-35 wt %, or 30-45 wt %, or 40-50 wt %.

In one embodiment, the MC1R peptide ligand for use in the methods described herein is selected from a group consisting of:

(SEQ ID NO: 2)
H-Tyr-Val-Leu-Gly-Pro-Phe-Arg-Trp-Asp-Arg-Phe-Gly-NH$_2$;

(SEQ ID NO: 3)
H-Tyr-Val-Leu-Gly-Pro-Phe-Arg-Phe-Asp-Arg-Phe-Gly-NH$_2$;

(SEQ ID NO: 4)
H-Tyr-Val-Leu-Gly-His-Phe-Leu-Trp-Asp-Arg-Phe-Gly-NH$_2$;

(SEQ ID NO: 5)
H-Tyr-Val-Leu-Gly-His-Phe-Leu-Phe-Asp-Arg-Phe-Gly-NH$_2$;

(SEQ ID NO: 6)
H-Tyr-Val-Leu-Gly-Pro-Phe-Leu-Trp-Asp-Arg-Phe-Gly-NH$_2$;

(SEQ ID NO: 7)
H-Tyr-Val-Leu-Gly-Pro-Phe-Leu-Phe-Asp-Arg-Phe-Gly-NH$_2$;

(SEQ ID NO: 8)
H-Tyr-Val-Leu-Gly-His-Phe-Arg-Trp-Asp-Arg-Phe-Gly-OH (SEQ ID NO: 9)
H-Tyr-Val-Leu-Gly-His-Phe-Arg-Trp-Asp-Arg-Phe-Gly-NH$_2$;
and (SEQ ID NO: 10)
H-Tyr-Val-Met-Gly-Pro-Phe-Arg-Trp-Asp-Arg-Phe-Gly-NH$_2$.

In another embodiment, the MC1R peptide ligand for use in the methods described herein is according to SEQ ID NO. 5.

(SEQ ID NO: 5)
H-Tyr-Val-Leu-Gly-His-Phe-Leu-Phe-Asp-Arg-Phe-Gly-NH$_2$.

According to yet another embodiment, the present invention features a photoprotective composition comprising a melanocortin 1 receptor (MC1R) peptide ligand, and one or more pharmaceutically acceptable excipients and/or diluents. In one embodiment, the MC1R peptide ligand comprises naturally occurring amino acids. The MC1R peptide ligand may be according to SEQ ID NO. 1:

(SEQ ID NO: 1)
H-Tyr$^1$-Val$^2$-Waa$^3$-Gly$^4$-Xaa$^5$-Phe$^6$-Yaa$^7$-Zaa$^8$-Asp$^9$-Arg$^{10}$-Phe$^{11}$-Gly$^{12}$-R1 wherein Waa is a Met, Ile, or Leu; Xaa is a His or Pro; Yaa is an Arg or Leu; Zaa is a Phe or Trp; and R1 of the C-terminal is —NH$_2$, or —OH; with the caveat that Waa is not Met, Xaa is not His, Yaa is not Arg, Zaa is not Trp, and R1 is not —OH simultaneously.

In some embodiments, the photoprotective composition is administered topically for topical or transdermal delivery of the MC1R peptide ligand through skin. Preferably, the MC1R peptide ligand is selective for, and is an agonist of MC1R for stimulating melanin production. The photoprotective composition can be in a form of a gel, a hydrogel, a water-in-oil emulsion, an oil-in-water emulsion, a cream, a lotion, an ointment, a spray, a foam, a multi-emulsion, or a liposome for topical administration.

In other embodiments, the amount of MC1R peptide ligand in the photoprotective composition ranges from about 0.001 to 50 wt %. For example, the amount of MC1R peptide ligand in the photoprotective composition can range from about 0.001-5 wt %, or 5-15 wt %, or 10-25 wt %, or 20-35 wt %, or 30-45 wt %, or 40-50 wt %.

In preferred embodiments, the MC1R peptide ligands described herein can induce melanin production. In other embodiments, the MC1R peptide ligand may be bioavailable for topical or transdermal delivery. In still other embodiments, the MC1R peptide ligand can promote natural pigmentation in skin. For example, the MC1R peptide ligand can stimulate eumelanin production for ultra-violet radiation protection of the skin.

In alternative embodiments, the MC1R peptide ligand may comprise an amino acid motif. For example, the amino acid motif may be a Pro-Phe-Arg-Trp, a Pro-Phe-Arg-Phe, a His-Phe-Leu-Trp, a His-Phe-Leu-Phe, a Pro-Phe-Leu-Trp, a Pro-Phe-Leu-Phe, or a His-Phe-Arg-Trp.

Another embodiment of the present invention features a modified melanocortin 1 receptor (MC1R) peptide ligand-micelle complex. The MC1R peptide ligand-micelle complex may comprise an MC1R peptide ligand comprising naturally occurring amino acids and a micelle comprising an inner core, outer core and hydrophilic shell. The MC1R peptide ligand can be any of the MC1R peptide ligands as described herein. In some embodiments, the MC1R peptide ligand can be linked to the shell of the micelle by a linker. The linker may comprise a 1,2,3-triazole, imine, disulfide, thioether, primary amide, or secondary amide. In other embodiments, the inner core of the micelle may comprise a hydrophobic polypeptide, the outer core may comprise a crosslinked peptide comprising a multiplicity of crosslinked amino acid residues, and the hydrophilic shell ma comprise a water soluble polymer. In still other embodiments, the inner core is covalently attached to the outer core and the outer core is covalently attached to the hydrophilic shell.

In accordance with the present invention, the synthesis of the derivatives is based on previous Structure Activity Relationship (SAR) of α-MSH to render γ-MSH more hMC1R-selective. Modification of the γ-MSH structure is focused on pharmacophore regions with naturally occurring amino acids to enhance receptor selectivity, stability, bioavailability.

Table 1 below shows non-limiting examples of sequences of γ-MSH derivative peptides. SEQ ID NOs. 11-15 are control peptides and SEQ ID NOs. 2-10 are non-limiting examples of new γ-MSH derivative peptides, in accordance with SEQ ID NO. 1, of the present invention. Exemplary quantities of the peptides that were synthesized are provided herein.

importance to achieve binding and receptor activation for the hMC3R and hMC4R. Similarly, a key interaction between the $Arg^8$ of the NDP-α-MSH and the $D^{154}$ as well as the $D^{158}$ of the hMC3R is necessary for binding.

Without wishing to limit the present invention to a particular theory or mechanism, the switching of the arginine in the tetrapeptide, His-Phe-Arg-Trp, to a neutrally charged

| SEQ ID NO. | Peptide Sequence | Weight (mg) |
|---|---|---|
| 2. $Leu^3$, $Pro^5$γ-MSH-NH$_2$ | H-Tyr-Val-Leu-Gly-Pro-Phe-Arg-Trp-Asp-Arg-Phe-Gly-NH$_2$ | 10 |
| 3. $Leu^3$, $Pro^5$, $Phe^6$γ-MSH-NH$_2$ | H-Tyr-Val-Leu-Gly-Pro-Phe-Arg-Phe-Asp-Arg-Phe-Gly-NH$_2$ | 5 |
| 4. $Leu^3$, $Leu^7$γ-MSH-NH$_2$ | H-Tyr-Val-Leu-Gly-His-Phe-Leu-Trp-Asp-Arg-Phe-Gly-NH$_2$ | 18 |
| 5. $Leu^3$, $Leu^7$, $Phe^8$γ-MSH-NH$_2$ | H-Tyr-Val-Leu-Gly-His-Phe-Leu-Phe-Asp-Arg-Phe-Gly-NH$_2$ | 10 |
| 6. $Leu^3$, $Pro^5Leu^7$γ-MSH-NH$_2$ | H-Tyr-Val-Leu-Gly-Pro-Phe-Leu-Trp-Asp-Arg-Phe-Gly-NH$_2$ | 5 |
| 7. $Leu^3$, $Pro^5Leu^7Phe^8$γ-MSH-NH$_2$ | H-Tyr-Val-Leu-Gly-Pro-Phe-Leu-Phe-Asp-Arg-Phe-Gly-NH$_2$ | 10 |
| 8. $Leu^3$γ-MSH | H-Tyr-Val-Leu-Gly-His-Phe-Arg-Trp-Asp-Arg-Phe-Gly-OH | 30 |
| 9. $Leu^3$γ-MSH-NH$_2$ | H-Tyr-Val-Leu-Gly-His-Phe-Arg-Trp-Asp-Arg-Phe-Gly-NH$_2$ | 5 |
| 10. $Pro^5$γ-MSH-NH$_2$ | H-Tyr-Val-Met-Gly-Pro-Phe-Arg-Trp-Asp-Arg-Phe-Gly-NH$_2$ | 100 |
| 11. $Nle^3$, $DNal^6$, $DTrp^8$γ-MSH | H-Tyr-Val-Nle-Gly-His-D-Nal(2')-Arg-D-Trp-Asp-Arg-Phe-Gly-NH$_2$ | NA |
| 12. Ac-NDP-γ-MSH-NH$_2$ | Ac-Tyr-Val-Nle-Gly-His-D-Phe-Arg-Trp-Asp-Arg-Phe-Gly-NH$_2$ | 18 |
| 13. γ-MSH | H-Tyr-Val-Met-Gly-His-Phe-Arg-Trp-Asp-Arg-Phe-Gly-OH | NA |
| 14. α-MSH | Ac-Ser-Tyr-Ser-Met-Glu-His-Phe-Arg-Trp-Gly-Lys-Pro-Val-NH$_2$ | 30 |
| 15. NDP-α-MSH | Ac-Ser-Tyr-Ser-Nle-Glu-His-D-Phe-Arg-Trp-Gly-Lys-Pro-Val-NH$_2$ | 20 |

Based on previous SAR studies and conformational based drug design studies, a series of γ-MSH peptides were designed with natural amino acids modifying the structure in the pharmacophore of γ-MSH. In Table 1, SEQ ID NO. 11, for example, is a peptide with exclusive agonist selectivity for the hMC1R. An Nle is replaced with an Ile in the entire group. To keep the conformation of the SEQ ID NO. 11, a β-like structure, a Pro was introduced in the $5^{th}$ position of γ-MSH. A Phe was also introduced in the $8^{th}$ position to enhance the selectivity of hMC1R. Finally, the C terminal amide group was applied to improve stability of this series of peptides.

Previous studies have demonstrated that the electrostatic interaction, Arg(L)-Asp(R), between the $Arg^8$ of the NDP-α-MSH and the Asp122, Asp126 of the hMC4R is of critical amino acid such as norleucine and leucine, can reduce binding towards the hMC3R and the hMC4R. Enhanced selectivity towards the MC1R can be reached with reduced electrostatic interaction between the $Arg^8(L)$-Asp(R) of the tetrapeptide and the respective aspartic acids on the MC3R and MC4R receptors. As shown in Table 4, Peptide 5, for example, has demonstrated significant selectivity towards hMC1R. By altering the $3^{rd}$ position of Met with Leu, the $7^{th}$ position of Arg with Leu, the 8th position of Trp with Phe, and the C-terminal amide of γ-MSH, the present invention have successfully produced a highly selective hMC1R ligand. This is an important and novel discovery using natural amino acids in linear MSH to enhance selectivity in critical to the prevention of skin cancer.

Table 2 shows binding affinities and cAMP activities of γ-MSH control peptides at hMCRs

| | hMC1R | | | hMC3R | | | hMC4R | | | hMC5R | | |
|---|---|---|---|---|---|---|---|---|---|---|---|---|
| no. | $^aIC_{50}$ (nM) | $^bEC_{50}$ (nM) | % max effect | $^aIC_{50}$ (nM) | $^bEC_{50}$ (nM) | % max effect | $^aIC_{50}$ (nM) | $^bEC_{50}$ (nM) | % max effect | $^aIC_{50}$ (nM) | $^bEC_{50}$ (nM) | % max effect |
| 11 | 0.30 ± 0.02 | 3.0 ± 0.2 | 70 | 5.0 ± 0.6 | 300 ± 6 | 6 | 6.0 ± 1 | 630 ± 70 | 18 | 3.5 ± 0.5 | NA | 6 |
| 10 | NA | NA | NA | 6.7 ± 1 | 0.33 ± 0.01 | 100 | 600 ± 70 | 100 ± 11 | 99 | 340 ± 40 | 82 ± 10 | 97 |
| 12 | 0.5 ± 0.01 | 1.5 ± 0.1 | 100 | 2. ± 0.02 | 2. ± 0.2 | 100 | 1.2 ± 0.2 | 1.4 ± 0.1 | 100 | 2.4 ± 0.3 | 1.9 ± 0.2 | 100 |
| 14 | 0.4 ± 0.01 | 0.7 ± 0.01 | 100 | 30 ± 3.9 | 6.7 ± 1 | 100 | 5 ± 1 | 2.1 ± 0.6 | 100 | 18 ± 2 | 8.1 ± 1.5 | 100 |
| 15 | 0.01 | 0.01 | 100 | 3.3 ± 0.3 | 0.8 ± 0.1 | 100 | 0.4 ± 0.02 | 0.2 ± 0.04 | 100 | 2.2 ± 0.5 | 1 ± 0.3 | 100 |

$^a$IC$_{50}$ = concentration of peptide at 50% specific binding (N = 4).
$^b$EC$_{50}$ = effective concentration of peptide that was able to generate 50% maximal intracellular cAMP accumulation (N = 4).
The peptides were tested at a range of concentration from $10^{-10}$ to $10^{-5}$ M.
NA, not available.

Methods

The following is a non-limiting example of synthesizing an MC1R peptide ligand according to an embodiment of the present invention.

1. Peptide Design and Synthesis.

N-Fmoc-amino acids were obtained from Bachem, NovaBiochem, and Advanced ChemTech. The side chain protecting groups were Boc and tBu [Fmoc-Asp(tBu)-OH, Fmoc-Trp(Boc)-OH, Fmoc-Arg(Boc)$_2$-OH, Fmoc-His (Boc)-OH, and Fmoc-Tyr(tBu)-OH]. Fmoc-Rink amide resin was purchased from Polymer Laboratories. Organic solvents and reagents were all purchased from Aldrich and used without further purification. All peptides were synthesized by the N-Fmoc solid-phase peptide strategy using DIC and HOBt as the coupling reagents.

Rink amide resin (100 mg, 0.065 mmol/g) was placed into the 5 mL polypropylene syringe with the frit on the bottom and swollen in DCM (2 mL) for 30 min and in DMF (2 mL) for 30 min. The Fmoc protecting group on the Rink is removed by 50% piperidine in DMF. After 20 min, the solution of piperidine was removed and the resin washed with DMF (2 mL, 10 times). N-Fmoc amino acid (3 equiv, 0.195 mmol) and HOBt (3 equiv, 0.195 mmol) were dissolved in 700 L of DMF, and then DIC (3 equiv, 0.195 mmol) was added. The coupling mixture was transferred into the syringe with the resin and shaken for 1-3 h. Coupling completion was monitored with a ninhydrin test.

The coupling mixture was removed and the resin mixed with DMF (2 mL, five times). N-Fmoc groups were removed with 50% piperidine in DMF over 20 min. Each coupling and deprotection step was repeated until a linear peptide was assembled. The final wash of the resin was done with DMF (2 mL, five times) and DCM (2 mL, five times). The product was cleaved from the resin with a mixture of 95% TFA, 2.5% TIPS, and 2.5% water during 1.5 h. Side chain protecting groups were removed during the cleavage step as well. The cleaved mixture was evaporated on a rotary evaporator, and the crude peptide was dissolved in acetic acid and purified by HPLC.

2. HPLC Purification

The peptide was lyophilized and purified by preparative RP-HPLC on a $C_{18}$ bonded silica column (Column YMC-Pack ODS-AM 150×4.6 mm, S-3 μm, 120 A) eluted with a linear gradient of acetonitrile (gradient, 2-80% B in A over 30 min, flow rate 0.8 mL/min. The HPLC column comprises YMC-Pack ODS-AM 150, 4.6 mm, S-3 im, 120A. The HPLC System 1 comprises solvent A, 0.1% TFA in water; solvent B, 0.1% TFA in 70% acetonitrile; gradient, 2-80% B in A over 30 min, flow rate 0.8 mL/min. HPLC System 2 comprises solvent A, 1% formic acid in water; solvent B, 1% formic acid in methanol; gradient, 2-80% B in A over 40 min, flow rate 0.8 mUmin. The TLC system 1 comprises CHC1$_3$/MeOH (4:1) and the TLC system 2, comprises CHC1$_3$/MeOH/AcOH (4:1:0.5). The results of the HPLC purification are shown in Table 3.

Table 3 shows the chemical characterizations including the MS and purity with HPLC.

| SEQ ID NO. | m/z calcd | m/z obsd | HPLC system 1 | HPLC system 2 | TLC system 1 | TLC system 2 |
|---|---|---|---|---|---|---|
| 2 | 1511.7 | 1511.7 | 11.4 | 16.8 | 0.02 | 0.09 |
| 3 | 1471.3 | 1471.7 | 11.6 | 16.2 | 0.04 | 0.18 |
| 4 | 1508.5 | 1508.7 | 11.2 | 16.1 | 0.01 | 0.04 |
| 5 | 1469.7 | 1469.7 | 12 | 17.8 | 0.1 | 0.32 |
| 6 | 1468.5 | 1468.7 | 12.4 | 17.9 | 0.11 | 0.39 |
| 7 | 1429.9 | 1429.7 | 11.8 | 16.7 | 0.1 | 0.32 |
| 8 | 1552.7 | 1552.7 | 11.3 | 16.2 | 0.03 | 0.13 |
| 9 | 1551.8 | 1551.7 | 11.4 | 16.4 | 0.06 | 0.21 |
| 10 | 1529.6 | 1529.7 | 11.6 | 16.5 | 0.07 | 0.23 |
| 12 | 1593.8 | 1593.8 | 11.3 | 16.5 | 0.04 | 0.17 |
| 14 | 1664.8 | 1664.7 | 11.4 | 16.7 | 0.01 | 0.04 |
| 15 | 1646.7 | 1646.8 | 11.2 | 16.5 | 0.04 | 0.17 |

3. Receptor Binding Assay

Competition binding experiments were carried out using both of cloned cell line and melanoma cells (A375, ATCC). The whole HEK293 cells were stably expressing human MC1, MC3, MC4, and MC5 receptors. HEK293 cells transfected with hMCRs were seeded on 96-well plates 48 hours before assay (50,000 cells/well). For the assay, the cell culture medium was aspirated and the cells were washed once with a freshly prepared minimum essencial medium (MEM) buffer containing 100% minimum essential medium with Earle's salt (MEM, GIBCO), and 25 mM sodium bicarbonate. Next, the cells were incubated for 40 min at 37° C. with different concentrations of unlabeled peptide and labeled [$^{125}$I]-[Nle$^4$, DPhe$^7$]-α-MSH (Perkin-Elmer Life Science, 20,000 cpm/well, 33.06 pM) diluted in a 125 μL of freshly prepared binding buffer containing 100% MEM, 25 mM HEPES (pH 7.4), 0.2% bovine serum albumin, 1 mM 1,10-phenanthrolone, 0.5 mg/L leupeptin, 200 mg/L bacitracin. The assay medium was subsequently removed, the cells were washed once with basic medium, and then lysed by the addition of 100 μL of 0.1M NaOH and 100 μL of 1% Triton X-100. The total labeled [$^{125}$I]-[Nle$^4$, Dphe$^7$]-α-MSH of lysed cells were measured by a Micro β-TriLux 1450 LSC and Luminescence Counter (PerkinElmer Life Science, Boston, Mass.) in Table 4.

Data Analysis $IC_{50}$ values represent the mean of two experiments performed in triplicate. $IC_{50}$ and $EC_{50}$ estimates and their associated standard errors were determined by fitting the data using a nonlinear least squares analysis, with the help of GraphPad Prism 5 (GraphPad Software, San Diego, Calif.). The $pA_2$ analysis is done by the Schild plot followed by the cAMP assay.

Table 4 shows the Binding affinity of novel designed γ-MSH analogues

| SEQ ID NO. | MC1R $IC_{50}$ (nM)* | % BE* | MC3R $IC_{50}$ (nM) | % BE | MC4R $IC_{50}$ (nM) | % BE | MC5R $IC_{50}$ (nM) | % BE |
|---|---|---|---|---|---|---|---|---|
| 2 | 43 | 100 | 165 | 100 | 76 | 100 | 67 | 100 |
| 3 | NB | 0 | 1252 | 33 | NB | 0 | NB | 0 |
| 4 | 1481 | 100 | 1881 | 26 | >10000 | 47 | 7.3 | 57 |
| 5 | 22 | 100 | >10000 | 45 | 3206 | 58 | NB | 0 |
| 6 | NB | 0 | 40 | 32 | 13 | 29 | 1.7 | 32 |

-continued

| SEQ ID NO. | MC1R IC$_{50}$ (nM)* | MC1R % BE* | MC3R IC$_{50}$ (nM) | MC3R % BE | MC4R IC$_{50}$ (nM) | MC4R % BE | MC5R IC$_{50}$ (nM) | MC5R % BE |
|---|---|---|---|---|---|---|---|---|
| 7 | 11 | 32 | 1399 | 47 | 58 | 36 | 5.3 | 34 |
| 9 | 198 | 100 | 1620 | 53 | 1021 | 100 | >10000 | 60 |

*IC$_{50}$ = concentration of peptide at 50% specific binding (N = 4). NB = 0% of $^{125}$I-NDP-α-MSH displacement observed at 10 μM. Percent Binding Efficiency (% BE) = maximal % of $^{125}$I-NDP-α-MSH displacement observed at 10 μM.

In alternative embodiments, unnatural amino acids, in addition to the natural amino acids, can be utilized in order to increase the selectivity of the MC1R peptide ligand to the hMC1R. As used herein, "unnatural amino acids", which can also be referred to as "modified amino acids" or "unusual amino acids", means amino acids that are not naturally encoded (i.e. non-proteinogenic) or found in the genetic code of any organisms. Typically, the unnatural amino acids are different from the twenty naturally occurring amino acids in their side chain functionality.

In some embodiments, the MC1R peptide ligand may comprise natural and unnatural amino acids. In an exemplary embodiment, the MC1R peptide ligand may be according to SEQ ID NO. 1:

(SEQ ID NO: 1)
H-Tyr$^1$-Val$^2$-Waa$^3$-Gly$^4$-Xaa$^5$-Phe$^6$-Yaa$^7$-Zaa$^8$-Asp$^9$-Arg$^{10}$-Phe$^{11}$-Gly$^{12}$-R1 wherein Waa is a Met, Ile, D-Ile, Leu, L-Norleucine (L-Nle), D-Nle, or L-2-Aminobutyric acid (L-Abu);

Xaa is a His, D-His, Pro, D-Pro, Pro(OH), NMe-His, 1-aminocyclopropane carboxylic acid (Acpc), 2-aminoindane-2-carboxylic acid (Aic), 1-amino-1-cyclohexane carboxylic acid (Che), 1-amino-1-cyclopentane carboxylic acid (Cpe), indoline-2-carboxyic acid (Ioc), octahydroindole-2-carboxylic acid (Oic), or tetrahydro-isoquinoline-3-carboxylic Acid (Tic);

Yaa is an Arg, Leu, Ile, Val, Abu, or Nle;

Zaa is a Phe, Trp, p-Phe, D-Phe, p-Me-Phe, Tyr-(OMe), 3-(1-Naphthyl)alanine (Nal(1')) or 3-(2-Naphthyl)alanine (Nal(2')); and R1 of the C-terminal is —NH$_2$, or —OH.

As defined herein, the term "N-methylation" refers to a form of alkylation wherein a methyl group, CH$_3$, replaces the hydrogen atom of the NH moiety in the backbone amide NHs of peptides. "NMe" preceding any three-letter abbreviation for an amino acid, i.e. NMe-His, denotes the N-methylated form of the amino acid.

As used herein, the term "about" refers to plus or minus 10% of the referenced number.

The disclosures of U.S. Patents and article publication are incorporated in their entirety by reference herein. All patents, patent applications, provisional applications, and publications referred to or cited herein, supra or infra, are incorporated by reference in their entirety, including all figures and tables, to the extent they are not inconsistent with the explicit teachings of this specification. Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A melanocortin 1 receptor (MC1R) peptide ligand comprising naturally occurring amino acids, wherein the MC1R peptide ligand is according to SEQ ID NO. 1:

(SEQ ID NO: 1)
H-Tyr$^1$-Val$^2$-Waa$^3$-Gly$^4$-Xaa$^5$-Phe$^6$-Yaa$^7$-Zaa$^8$-Asp$^9$-Arg$^{10}$-Phe$^{11}$-Gly$^{12}$-R1 wherein Waa is a Met, Ile, or Leu, Xaa is a His or Pro, Yaa is an Arg or Leu, and Zaa is a Phe or Trp, and wherein R1 of the C-terminal is —NH$_2$, or —OH, with the caveat that Waa is not Met, Xaa is not His, Yaa is not Arg, Zaa is not Trp, and R1 is not OH simultaneously.

2. The MC1R peptide ligand according to claim 1, wherein Waa is Leu, Xaa is His, Yaa is Leu, Zaa is Phe, and R1 is —NH$_2$.

3. The MC1R peptide ligand according to claim 1, wherein the MC1R peptide ligand is selected from a group consisting of:

(SEQ ID NO: 2)
H-Tyr-Val-Leu-Gly-Pro-Phe-Arg-Trp-Asp-Arg-Phe-Gly-NH$_2$;

(SEQ ID NO: 5)
H-Tyr-Val-Leu-Gly-His-Phe-Leu-Phe-Asp-Arg-Phe-Gly-NH$_2$;

(SEQ ID NO: 6)
H-Tyr-Val-Leu-Gly-Pro-Phe-Leu-Trp-Asp-Arg-Phe-Gly-NH$_2$;

(SEQ ID NO: 7)
H-Tyr-Val-Leu-Gly-Pro-Phe-Leu-Phe-Asp-Arg-Phe-Gly-NH$_2$;

(SEQ ID NO: 8)
H-Tyr-Val-Leu-Gly-His-Phe-Arg-Trp-Asp-Arg-Phe-Gly-OH

-continued (SEQ ID NO: 9)
H-Tyr-Val-Leu-Gly-His-Phe-Arg-Trp-Asp-Arg-Phe-Gly-NH$_2$;
and (SEQ ID NO: 10)
H-Tyr-Val-Met-Gly-Pro-Phe-Arg-Trp-Asp-Arg-Phe-Gly-NH$_2$.

4. The MC1R peptide ligand of claim 1, wherein the MC1R peptide ligand is selective for MC1R, wherein the MC1R peptide ligand is an agonist of MC1R.

5. The MC1R peptide ligand of claim 1, wherein the MC1R peptide ligand is at least twice as selective for MC1R than MC3R, MC4R, or MC5R.

6. The MC1R peptide ligand of claim 1, wherein the MC1R peptide ligand is capable of stimulating melanin production.

7. A pharmaceutical composition for preventing skin cancer, said composition comprising a melanocortin 1 receptor (MC1R) peptide ligand in a pharmaceutically acceptable carrier, wherein the MC1R peptide ligand comprises naturally occurring amino acids, wherein the MC1R peptide ligand is according to SEQ ID NO. 1:

(SEQ ID NO: 1)
H-Tyr$^1$-Val$^2$-Waa$^3$-Gly$^4$-Xaa$^5$-Phe$^6$-Yaa$^7$-Zaa$^8$-Asp$^9$-Arg$^{10}$-Phe$^{11}$-Gly$^{12}$-R1 wherein Waa is a Met, Ile, or Leu, Xaa is a His or Pro, Yaa is an Arg or Leu, and Zaa is a Phe or Trp, and wherein R1 of the C-terminal is —NH$_2$, or —OH, with the caveat that Waa is not Met, Xaa is not His, Yaa is not Arg, Zaa is not Trp, and R1 is not OH simultaneously, and wherein the MC1R peptide ligand is selective for MC1R, and wherein the MC1R peptide ligand is an agonist of MC1R, wherein the MC1R peptide ligand is capable of stimulating melanin production, thereby preventing skin cancer.

8. A pharmaceutical composition for stimulating melanin production, said composition comprising a melanocortin 1 receptor (MC1R) peptide ligand in a pharmaceutically acceptable carrier, wherein the MC1R peptide ligand comprises naturally occurring amino acids, wherein the MC1R peptide ligand is according to SEQ ID NO. 1:

(SEQ ID NO: 1)
H-Tyr$^1$-Val$^2$-Waa$^3$-Gly$^4$-Xaa$^5$-Phe$^6$-Yaa$^7$-Zaa$^8$-Asp$^9$-Arg$^{10}$-Phe$^{11}$-Gly$^{12}$-R1 wherein Waa is a Met, Ile, or Leu, Xaa is a His or Pro, Yaa is an Arg or Leu, and Zaa is a Phe or Trp, and wherein R1 of the C-terminal is —NH$_2$, or —OH, with the caveat that Waa is not Met, Xaa is not His, Yaa is not Arg, Zaa is not Trp, and R1 is not —OH simultaneously, and wherein the MC1R peptide ligand is selective for MC1R, and wherein the MC1R peptide ligand is an agonist of MC1R, wherein the MC1R peptide ligand is capable of stimulating melanin production.

9. The pharmaceutical composition of claim 7, wherein the MC1R peptide ligand is present in an amount ranging from about 0.001-20 wt % of the pharmaceutical composition.

10. The pharmaceutical composition of claim 7, wherein the pharmaceutical composition is administered topically for delivering the MC1R peptide ligand through skin.

11. The pharmaceutical composition according to claim 10, wherein the pharmaceutical composition is in a form selected from a group consisting of a gel, a hydrogel, a water-in-oil emulsion, an oil-in-water emulsion, a cream, a lotion, an ointment, a spray, a foam, a multi-emulsion, and a liposome.

12. The pharmaceutical composition according to claim 10, wherein the pharmaceutical composition is in a form of a patch, said patch comprising an impenetrable outer layer, and a permeable inner layer, wherein the outer layer and the inner layer form a reservoir for storing the pharmaceutical composition, wherein when the patch is applied on a skin of mammal, the pharmaceutical composition permeates through the inner layer and the MC1R peptide ligand pass through the skin.

13. The pharmaceutical compositions of claim 7, wherein the MC1R peptide ligand is selected from a group consisting of:

(SEQ ID NO: 2)
H-Tyr-Val-Leu-Gly-Pro-Phe-Arg-Trp-Asp-Arg-Phe-Gly-NH$_2$;

(SEQ ID NO: 5)
H-Tyr-Val-Leu-Gly-His-Phe-Leu-Phe-Asp-Arg-Phe-Gly-NH$_2$;

(SEQ ID NO: 7)
H-Tyr-Val-Leu-Gly-Pro-Phe-Leu-Phe-Asp-Arg-Phe-Gly-NH$_2$;

(SEQ ID NO: 8)
H-Tyr-Val-Leu-Gly-His-Phe-Arg-Trp-Asp-Arg-Phe-Gly-OH (SEQ ID NO: 9)
H-Tyr-Val-Leu-Gly-His-Phe-Arg-Trp-Asp-Arg-Phe-Gly-NH$_2$;
and (SEQ ID NO: 10)
H-Tyr-Val-Met-Gly-Pro-Phe-Arg-Trp-Asp-Arg-Phe-Gly-NH$_2$.

14. The pharmaceutical composition of claim 8, wherein the MC1R peptide ligand is present in an amount ranging from about 0.001-20 wt % of the pharmaceutical composition.

15. The pharmaceutical composition of claim 8, wherein the pharmaceutical composition is administered topically for delivering the MC1R peptide ligand through skin.

16. The pharmaceutical composition of claim 15, wherein the pharmaceutical composition is in a form selected from a group consisting of a gel, a hydrogel, a water-in-oil emulsion, an oil-in-water emulsion, a cream, a lotion, an ointment, a spray, a foam, a multi-emulsion, and a liposome.

17. The pharmaceutical composition of claim 15, wherein the pharmaceutical composition is in a form of a patch, said patch comprising an impenetrable outer layer, and a permeable inner layer, wherein the outer layer and the inner layer form a reservoir for storing the pharmaceutical composition, wherein when the patch is applied on a skin of mammal, the pharmaceutical composition permeates through the inner layer and the MC1R peptide ligand pass through the skin.

18. The pharmaceutical composition of claim 8, wherein the MC1R peptide ligand is selected from a group consisting of:

(SEQ ID NO: 2)
H-Tyr-Val-Leu-Gly-Pro-Phe-Arg-Trp-Asp-Arg-Phe-Gly-NH₂;

(SEQ ID NO: 5)
H-Tyr-Val-Leu-Gly-His-Phe-Leu-Phe-Asp-Arg-Phe-Gly-NH₂;

(SEQ ID NO: 7)
H-Tyr-Val-Leu-Gly-Pro-Phe-Leu-Phe-Asp-Arg-Phe-Gly-NH₂;

(SEQ ID NO: 8)
H-Tyr-Val-Leu-Gly-His-Phe-Arg-Trp-Asp-Arg-Phe-Gly-OH (SEQ ID NO: 9)
H-Tyr-Val-Leu-Gly-His-Phe-Arg-Trp-Asp-Arg-Phe-Gly-NH₂;

and (SEQ ID NO: 10)
H-Tyr-Val-Met-Gly-Pro-Phe-Arg-Trp-Asp-Arg-Phe-Gly-NH₂.

19. A method of preventing skin cancer in a mammal, said method comprising administering to the mammal a therapeutically effective amount of a melanocortin 1 receptor (MC1R) peptide ligand according to claim 1, wherein the MC1R peptide ligand is selective for MC1R, wherein the MC1R peptide ligand is capable of stimulating melanin production, thereby preventing skin cancer.

20. A method of stimulating melanin production in a mammal, said method comprising administering to the mammal a melanocortin 1 receptor (MC1R) peptide ligand according to claim 1 in an amount sufficient to stimulate melanin production, wherein the MC1R peptide ligand is selective for MC1R.

* * * * *

SEQUENCE LISTING

```
<160> NUMBER OF SEQ ID NOS: 15

<210> SEQ ID NO 1
<211> LENGTH: 12
<212> TYPE: PRT
<213> ORGANISM: Artificial Sequence
<220> FEATURE:
<223> OTHER INFORMATION: modifed derivative of gamma-melanocyte-
      stimulating hormone (gamma-MSH)
<220> FEATURE:
<221> NAME/KEY: MISC_FEATURE
<222> LOCATION: (3)..(3)
<223> OTHER INFORMATION: natural or unnatural amino acid
<220> FEATURE:
<221> NAME/KEY: MISC_FEATURE
<222> LOCATION: (5)..(5)
<223> OTHER INFORMATION: natural or unnatural amino acid
<220> FEATURE:
<221> NAME/KEY: MISC_FEATURE
```

```
<222> LOCATION: (7)..(7)
<223> OTHER INFORMATION: natural or unnatural amino acid
<220> FEATURE:
<221> NAME/KEY: MISC_FEATURE
<222> LOCATION: (8)..(8)
<223> OTHER INFORMATION: natural or unnatural amino acid
<220> FEATURE:
<221> NAME/KEY: MISC_FEATURE
<222> LOCATION: (12)..(12)
<223> OTHER INFORMATION: optional C-terminal modification

<400> SEQUENCE: 1

Tyr Val Xaa Gly Xaa Phe Xaa Xaa Asp Arg Phe Gly
 1               5                  10

<210> SEQ ID NO 2
<211> LENGTH: 12
<212> TYPE: PRT
<213> ORGANISM: Artificial Sequence
<220> FEATURE:
<223> OTHER INFORMATION: modfed derivative of gamma-MSH
<220> FEATURE:
<221> NAME/KEY: MOD_RES
<222> LOCATION: (12)..(12)
<223> OTHER INFORMATION: AMIDATION

<400> SEQUENCE: 2

Tyr Val Leu Gly Pro Phe Arg Trp Asp Arg Phe Gly
 1               5                  10

<210> SEQ ID NO 3
<211> LENGTH: 12
<212> TYPE: PRT
<213> ORGANISM: Artificial Sequence
<220> FEATURE:
<223> OTHER INFORMATION: modfed derivative of gamma-MSH
<220> FEATURE:
<221> NAME/KEY: MOD_RES
<222> LOCATION: (12)..(12)
<223> OTHER INFORMATION: AMIDATION

<400> SEQUENCE: 3

Tyr Val Leu Gly Pro Phe Arg Phe Asp Arg Phe Gly
 1               5                  10

<210> SEQ ID NO 4
<211> LENGTH: 12
<212> TYPE: PRT
<213> ORGANISM: Artificial Sequence
<220> FEATURE:
<223> OTHER INFORMATION: modfed derivative of gamma-MSH
<220> FEATURE:
<221> NAME/KEY: MOD_RES
<222> LOCATION: (12)..(12)
<223> OTHER INFORMATION: AMIDATION

<400> SEQUENCE: 4

Tyr Val Leu Gly His Phe Leu Trp Asp Arg Phe Gly
 1               5                  10

<210> SEQ ID NO 5
<211> LENGTH: 12
<212> TYPE: PRT
<213> ORGANISM: Artificial Sequence
<220> FEATURE:
<223> OTHER INFORMATION: modfed derivative of gamma-MSH
<220> FEATURE:
<221> NAME/KEY: MOD_RES
<222> LOCATION: (12)..(12)
<223> OTHER INFORMATION: AMIDATION
```

```
<400> SEQUENCE: 5

Tyr Val Leu Gly His Phe Leu Phe Asp Arg Phe Gly
1               5                   10

<210> SEQ ID NO 6
<211> LENGTH: 12
<212> TYPE: PRT
<213> ORGANISM: Artificial Sequence
<220> FEATURE:
<223> OTHER INFORMATION: modifed derivative of gamma-MSH
<220> FEATURE:
<221> NAME/KEY: MOD_RES
<222> LOCATION: (12)..(12)
<223> OTHER INFORMATION: AMIDATION

<400> SEQUENCE: 6

Tyr Val Leu Gly Pro Phe Leu Trp Asp Arg Phe Gly
1               5                   10

<210> SEQ ID NO 7
<211> LENGTH: 12
<212> TYPE: PRT
<213> ORGANISM: Artificial Sequence
<220> FEATURE:
<223> OTHER INFORMATION: modifed derivative of gamma-MSH
<220> FEATURE:
<221> NAME/KEY: MOD_RES
<222> LOCATION: (12)..(12)
<223> OTHER INFORMATION: AMIDATION

<400> SEQUENCE: 7

Tyr Val Leu Gly Pro Phe Leu Phe Asp Arg Phe Gly
1               5                   10

<210> SEQ ID NO 8
<211> LENGTH: 12
<212> TYPE: PRT
<213> ORGANISM: Artificial Sequence
<220> FEATURE:
<223> OTHER INFORMATION: modifed derivative of gamma-MSH

<400> SEQUENCE: 8

Tyr Val Leu Gly His Phe Arg Trp Asp Arg Phe Gly
1               5                   10

<210> SEQ ID NO 9
<211> LENGTH: 12
<212> TYPE: PRT
<213> ORGANISM: Artificial Sequence
<220> FEATURE:
<223> OTHER INFORMATION: modifed derivative of gamma-MSH
<220> FEATURE:
<221> NAME/KEY: MOD_RES
<222> LOCATION: (12)..(12)
<223> OTHER INFORMATION: AMIDATION

<400> SEQUENCE: 9

Tyr Val Leu Gly His Phe Arg Trp Asp Arg Phe Gly
1               5                   10

<210> SEQ ID NO 10
<211> LENGTH: 12
<212> TYPE: PRT
<213> ORGANISM: Artificial Sequence
<220> FEATURE:
<223> OTHER INFORMATION: modifed derivative of gamma-MSH
<220> FEATURE:
<221> NAME/KEY: MOD_RES
<222> LOCATION: (12)..(12)
```

```
<223> OTHER INFORMATION: AMIDATION

<400> SEQUENCE: 10

Tyr Val Met Gly Pro Phe Arg Trp Asp Arg Phe Gly
1               5                   10

<210> SEQ ID NO 11
<211> LENGTH: 12
<212> TYPE: PRT
<213> ORGANISM: Artificial Sequence
<220> FEATURE:
<223> OTHER INFORMATION: modifed derivative of gamma-MSH
<220> FEATURE:
<221> NAME/KEY: MISC_FEATURE
<222> LOCATION: (3)..(3)
<223> OTHER INFORMATION: Norleucine
<220> FEATURE:
<221> NAME/KEY: MISC_FEATURE
<222> LOCATION: (6)..(6)
<223> OTHER INFORMATION: D-Nal(2')
<220> FEATURE:
<221> NAME/KEY: MISC_FEATURE
<222> LOCATION: (8)..(8)
<223> OTHER INFORMATION: D-Trp
<220> FEATURE:
<221> NAME/KEY: MOD_RES
<222> LOCATION: (12)..(12)
<223> OTHER INFORMATION: AMIDATION

<400> SEQUENCE: 11

Tyr Val Leu Gly His Xaa Arg Trp Asp Arg Phe Gly
1               5                   10

<210> SEQ ID NO 12
<211> LENGTH: 12
<212> TYPE: PRT
<213> ORGANISM: Artificial Sequence
<220> FEATURE:
<223> OTHER INFORMATION: modifed derivative of gamma-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Norleucine
<220> FEATURE:
<221> NAME/KEY: MISC_FEATURE
<222> LOCATION: (6)..(6)
<223> OTHER INFORMATION: D-Phe
<220> FEATURE:
<221> NAME/KEY: MOD_RES
<222> LOCATION: (12)..(12)
<223> OTHER INFORMATION: AMIDATION

<400> SEQUENCE: 12

Tyr Val Leu Gly His Phe Arg Trp Asp Arg Phe Gly
1               5                   10

<210> SEQ ID NO 13
<211> LENGTH: 12
<212> TYPE: PRT
<213> ORGANISM: Artificial Sequence
<220> FEATURE:
<223> OTHER INFORMATION: gamma-melanocyte-stimulating hormone
      (gamma-MSH)

<400> SEQUENCE: 13

Tyr Val Met Gly His Phe Arg Trp Asp Arg Phe Gly
1               5                   10
```

```
<210> SEQ ID NO 14
<211> LENGTH: 13
<212> TYPE: PRT
<213> ORGANISM: Artificial Sequence
<220> FEATURE:
<223> OTHER INFORMATION: alpha-melanocyte-stimulating hormone
      (alpha-MSH)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: AMIDATION

<400> SEQUENCE: 14

Ser Tyr Ser Met Gly His Phe Arg Trp Gly Lys Pro Val
1               5                   10

<210> SEQ ID NO 15
<211> LENGTH: 13
<212> TYPE: PRT
<213> ORGANISM: Artificial Sequence
<220> FEATURE:
<223> OTHER INFORMATION: modifed derivative of alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Norleucine
<220> FEATURE:
<221> NAME/KEY: MISC_FEATURE
<222> LOCATION: (7)..(7)
<223> OTHER INFORMATION: D-Phe
<220> FEATURE:
<221> NAME/KEY: MOD_RES
<222> LOCATION: (13)..(13)
<223> OTHER INFORMATION: AMIDATION

<400> SEQUENCE: 15

Ser Tyr Ser Leu Gly His Phe Arg Trp Gly Lys Pro Val
1               5                   10
```